United States Patent [19]

Atkinson

[11] Patent Number: 4,561,431
[45] Date of Patent: Dec. 31, 1985

[54] LAVAGE SYSTEM WITH LINEAR MOTOR

[75] Inventor: Robert W. Atkinson, Dover, Ohio

[73] Assignee: Snyder Laboratories, Inc., Dover, Ohio

[21] Appl. No.: 445,797

[22] Filed: Dec. 1, 1982

[51] Int. Cl.[4] .............................................. A61H 7/00
[52] U.S. Cl. ................................................... 128/66
[58] Field of Search ........................... 128/66; 604/30; 239/102; 433/229

[56] References Cited

U.S. PATENT DOCUMENTS

| | | | |
|---|---|---|---|
| Re. 20,510 | 9/1937 | Green | 172/126 |
| 524,044 | 8/1894 | Merritt et al. | |
| 1,995,424 | 3/1935 | Guinness | 138/66 |
| 2,669,937 | 2/1954 | Presentey | 417/413 |
| 3,433,983 | 3/1969 | Keistman et al. | 310/15 |
| 3,448,303 | 6/1969 | Thorel et al. | 310/14 |
| 3,540,437 | 11/1970 | Troy | 128/66 |
| 3,863,082 | 1/1975 | Gillott et al. | 310/27 |
| 3,910,266 | 10/1975 | Kawase | 128/66 |
| 3,912,168 | 10/1975 | Mullins et al. | 239/102 |
| 3,917,987 | 11/1975 | Inoue | 318/135 |
| 3,952,376 | 4/1976 | Moret et al. | 128/66 |
| 3,982,540 | 9/1976 | Ross | 128/278 |
| 3,993,054 | 11/1976 | Newman | 128/66 |
| 4,101,950 | 7/1978 | Hager et al. | 361/203 |
| 4,215,476 | 8/1980 | Armstrong | 433/80 |
| 4,278,078 | 7/1981 | Smith | 128/66 |
| 4,282,873 | 8/1981 | Roth | 128/276 |
| 4,294,251 | 10/1981 | Greenwald et al. | 128/276 |
| 4,299,221 | 11/1981 | Phillips et al. | 128/276 |
| 4,350,477 | 9/1982 | Mazal | 417/384 |

FOREIGN PATENT DOCUMENTS 1602277  11/1981  United Kingdom.

OTHER PUBLICATIONS

Stryker ® Pamphlet, "SysTec TM 280 Suction/Irrigation Nitrogen Power System.
Stryker ® Manual "SysTec TM 280.

*Primary Examiner*—Gene Mancene
*Assistant Examiner*—Wenceslao J. Contreras
*Attorney, Agent, or Firm*—Paul David Schoenle

[57] ABSTRACT

A linear motor drives a reciprocating pump to produce a flow of lavage fluid. In the preferred embodiment the motor is a moving coil linear motor and the coil is attached to one plate of a drive member comprising a pair of circular plates connected by three shafts that slide in bearings passing through the motor core. Springs having varying coil spacing are seated between the plates and motor core to variably damp the motor's motion, with the strongest damping at the ends of its reciprocating stroke.

12 Claims, 29 Drawing Figures

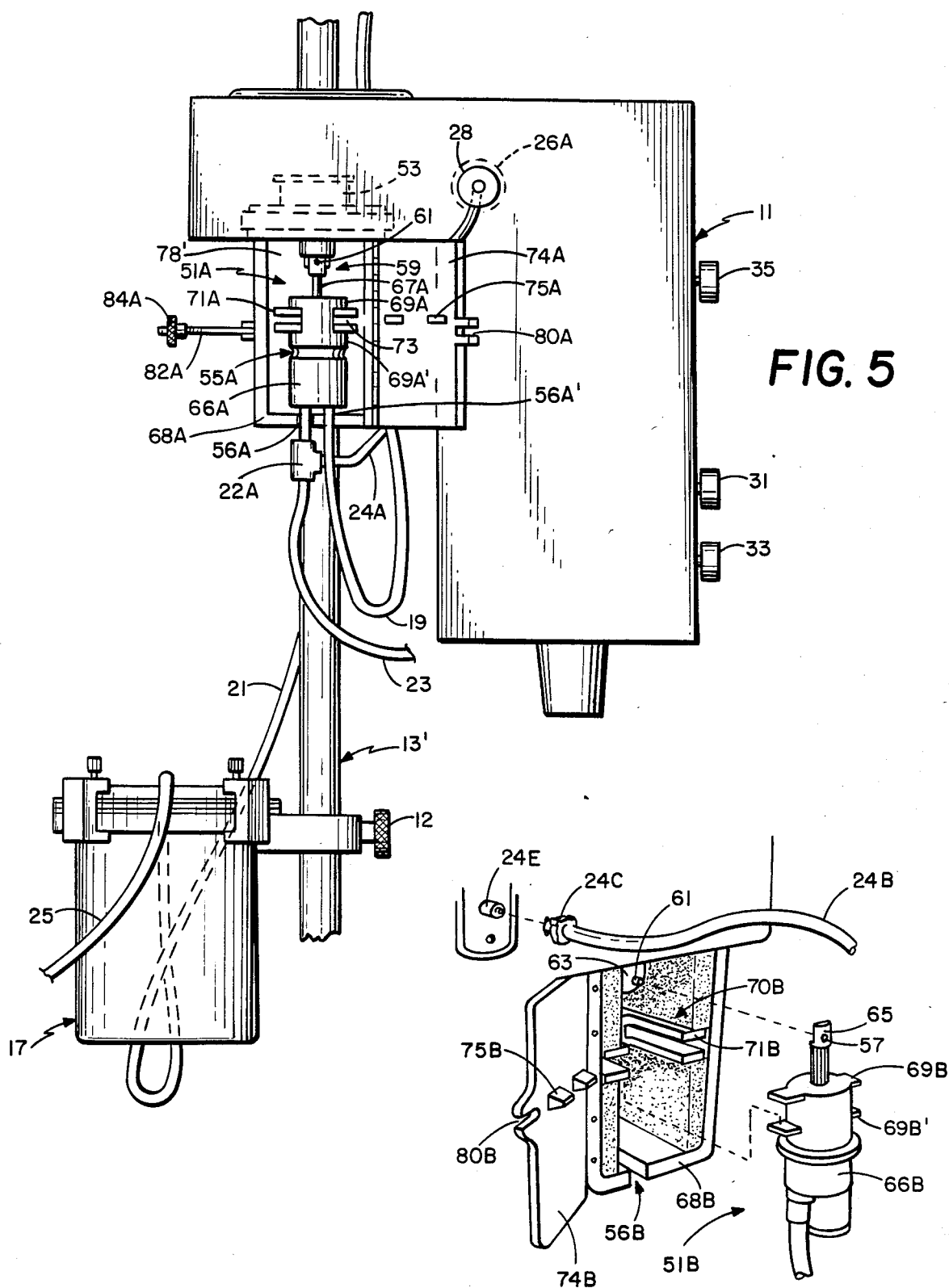

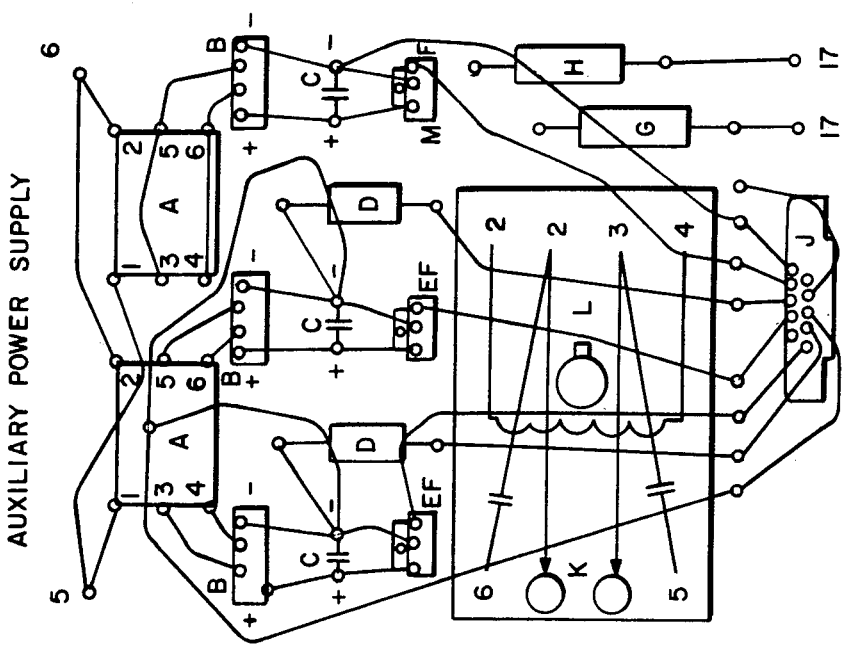
FIG. IIC

SUCTION OSCILLATOR COMPONENTS

A CONNECTOR WTB10PR7JTA
B 10μF 50V AXIAL CAPACITOR
C 1μF 35V AXIAL CAPACITOR
D XR2206CP-2 CHIP
E 16 PIN SOCKET
F 10μF 16V RADIAL CAPACITOR
G 30 K RESISTOR
H 1 K RESISTOR
J 300 OHM RESISTOR
K 10 K RESISTOR
L 68 K RESISTOR
M 100 K RESISTOR
N 1 MEG 1 TURN POT
P 50K 1 TURN POT
Q 1K 1 TURN POT
R 50 K 15 TURN POT
S 100 K 15 TURN POT

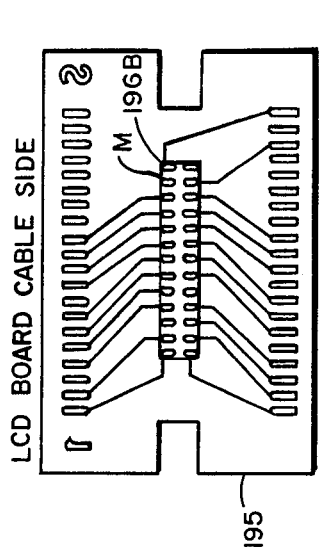
FIG.11K₁
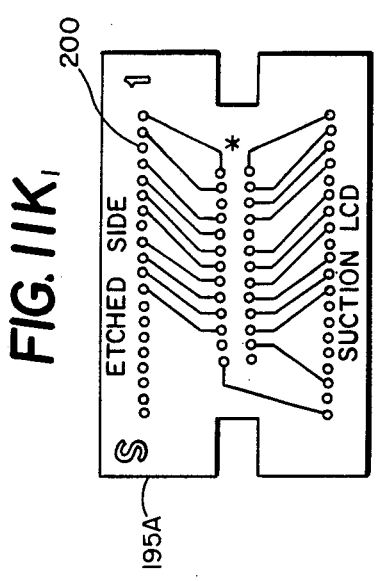
FIG.11K₂
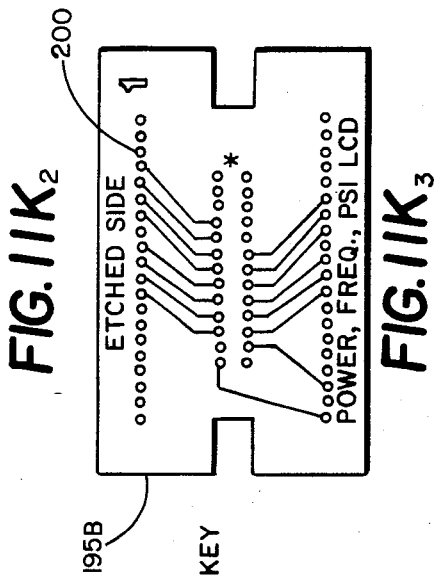
FIG.11K₃
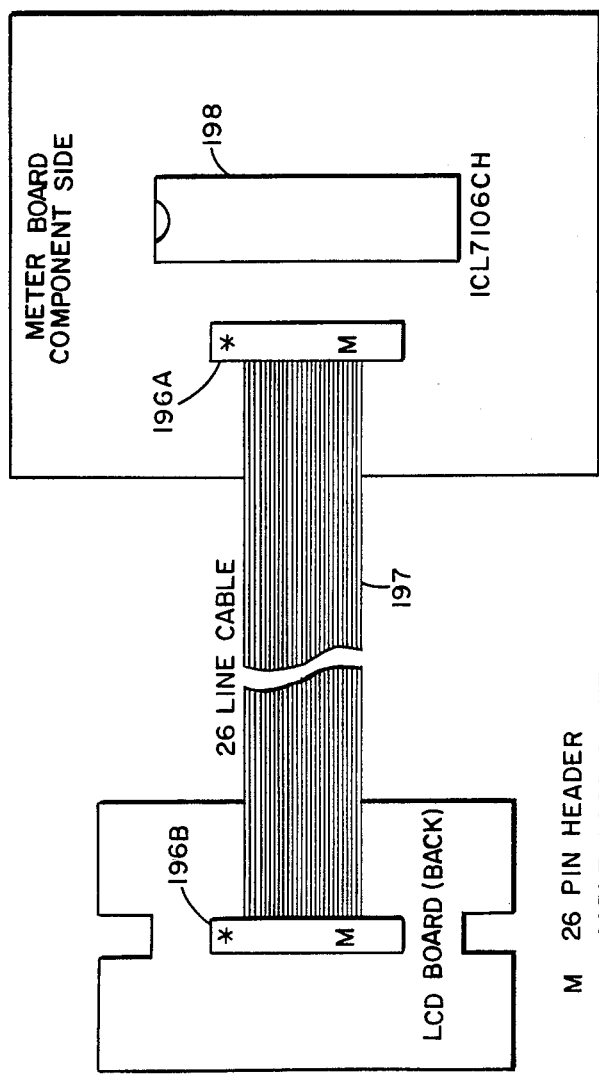
FIG.11J₁
M  26 PIN HEADER
*  CABLE LOCATOR KEY
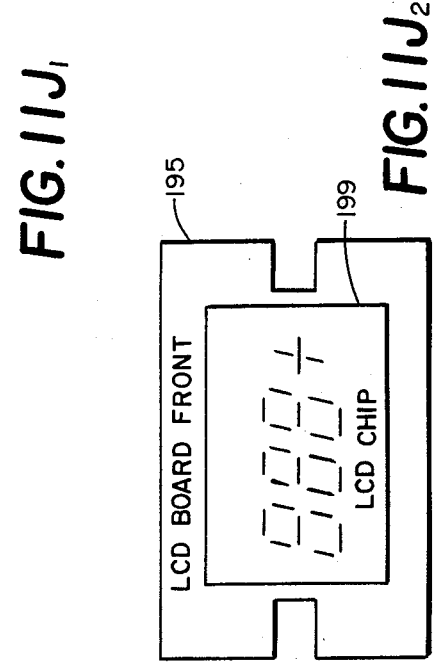
FIG.11J₂

SUCTION TRANSDUCER COMPONENTS

A. FOXBORO 1800 TRANSDUCER
B. BALANCE RESISTOR

LAVAGE SYSTEM WITH LINEAR MOTOR

BACKGROUND OF THE INVENTION

1. Field of the Invention

The invention in general relates to the field of medical, dental and therapeutic lavage, and more particularly to a mechanized lavage system having a fluid pump driven by an electric motor.

2. Description of the Prior Art

Lavage, or the washing of tissue, is perhaps as old as medicine itself. In the early years it consisted of the application of fluid, generally a liquid such as water, to tissue to wash away dirt or debris. In more modern times, it has become more important, and more thorough, due to an awareness of bacteria and other organisms that may cause infection. In the last several decades, mechanized lavage systems have become common.

Before proceeding to the discussion of prior art mechanized devices it will be useful to clarify terminology. The word "lavage" is used ambiguously in the literature, sometimes referring to a pulsating stream type washing or therapy, sometimes referring to a stream type of washing, and sometimes also including an aspiration function. In this document, unless the context clearly indicates otherwise, "irrigation" shall mean the stream type of washing "pulsatile lavage" shall mean the pulsating type of washing or therapy, and the word "lavage" shall mean the broadest sense of the term, referring to any one of, or combinations of, irrigation, pulsatile lavage, and aspiration.

U.S. Pat. No. 3,540,437 issued to Seymour Troy and U.S. Pat. No. 4,278,078 issued to William E. Smith, illustrate lavage systems in which the fluid stream for irrigation or pulsatile lavage is produced by a reciprocating pump. The former patent gives no indication of the type of motor which may be used for driving the reciprocating pump, while the latter patent discloses a rotary gas-driven motor as the pump driving means. It appears that these prior art reciprocating pump systems have not been very successful; an analysis of the system of U.S. Pat. No. 3,540,437 indicates that the pulsation produced would be either very weak or nonexistent, while it appears that the system of U.S. Pat. No. 4,278,078 would be very inefficient.

U.S. Pat. Nos. 3,912,168 issued to Keith M. Mullins et al and 3,993,054 issued to Gordon Arthur Newman, disclose lavage systems incorporating a peristaltic pump driven by a rotary electric motor. These peristaltic type systems in general appear to have been more successful than the above-cited reciprocating systems. However, it is noted that none of these systems appear to be frequency controlled. Further, it appears that the only volume controls disclosed in any of the lavage systems are throttle type controls, which are inherently inefficient. Despite these limitations, the peristaltic motor, at the time of the conception of the present invention has been the motor of choice in lavage systems, due to the small size of the lavage systems using such motors and the easy replaceability, sterilizability and the disposability of its pumping chamber. These two features are essential for commercial success of a medical, dental or therapeutic lavage system.

Up to the present time, moving coil electrical motors have been thought to be unsuitable for medical, dental and therapeutic lavage systems Generally, moving coil linear motors have been associated with functions requiring rapid response and small forces. Typical applications have been loudspeakers, or the movement of magnetic heads or pens in information processing systems See for example U.S. Pat. No. 3,917,987 issued to Yuji Inoue. Whenever moving coil type linear motors have been used for functions requiring a force as significant as required in a lavage system, very large motors have been designed. See, for example, U.S. Pat. Nos. 524,044 issued to Frank W. Merritt et al and 3,863,082 issued to Donald H. Gillott et al. The latter patent relates to a linear motor for use in a respirator requiring forces on the same order generally required for lavage systems. The size of the motor disclosed is about 14 inches long by 12 inches in diameter. The support system, drive system and cooling system of the motor of course would add considerably to the size. Thus any person skilled in the art of lavage systems would immediately reject such a motor for use in this field. The only disclosure known to the applicant which suggests the use of a small moving coil linear motor for fluid pumping purposes is U.S. Pat. No. 2,669,937 issued to Shelly Presentey. However, the motor disclosed is clearly unsuitable for use in a lavage system. Moreover, the patent does not appear to disclose an actual use in any fluid pumping function, Further, the disclosure explicitly calls for elimination of all mechanical members such as shafts, journals, bearings and the like, which, as will be seen below, is directly contrary to the present invention.

Linear motors having stationary coils and moving magnets have apparently been used for pumping liquids. See, for example U.S. Pat. Nos. 3,423,983 issued to A. R. Keistman et al, 4,101,950 issued to Donald L. Hager et al, and Re. 20,510 issued to H. V. Green. Each of these patents is used for a function requiring considerably less force and lower usage requirements than required in a lavage system. Thus up to the present time no linear motor, either of the moving coil type or the moving magnet type, have ever been used in a lavage system.

SUMMARY OF THE INVENTION

It is an object of this invention to provide a medical, dental or therapeutic lavage system powered by a linear motor. Another object is to provide the above object with a lavage system that utilizes a moveable coil motor.

It is another object of the invention to provide a lavage system with such a motor incorporating a journal comprising a shaft moving in a bearing.

Yet another object of the invention is to provide a lavage system that provides one or more of the above objects and which can be routinely used in situations requiring a sterile fluid flow.

A further object of the invention is to provide a lavage system that includes one or more of the preceding objects in a lavage system in which the frequency is easily controllable to high accuracy.

The invention provides a medical, dental or therapeutic lavage apparatus comprising a chamber having an inlet port and an outlet port, a reciprocating means for imparting a pulsatile flow to liquid moving from said inlet port to said outlet port, a linear electric motor having a drive member, a means for supporting the motor and the chamber in a stable relationship, and a means for connecting the motor drive member to the reciprocating means so that the motion of the drive member is transferred to the reciprocating means to produce the pulsatile flow. Preferably, the motor includes a moveable coil and a stationary motor core, and the motor drive member includes a shaft and a bearing, with the shaft moveable in the bearing Preferably, the shaft passes through the motor core, In the preferred embodiment, there are three such shafts and bearings and the drive means includes a first plate to which the coil and one end of each of the shafts are connected, a second plate to which the other ends of the shafts are connected, and the shafts are spaced apart along a circle about the axis of the coil. Preferably, the motor includes a means for variably damping the motion of the coil which provides minimum damping when the coil is positioned at or near the center of its reciprocating path and maximum damping when the coil is located at or near the end points of its motion in either direction. The preferred embodiment also includes means for producing an electrical power signal and for applying the signal to the motor, and a means for varying the frequency and amplitude of the power signal including manually settable frequency and amplitude controls In another aspect the invention provides a lavage apparatus comprising a disposable chamber having an inlet port and an outlet port, a reciprocating means for imparting a fluid flow to liquid moving from the inlet port to the outlet port, a linear motor having a drive member, a means for supporting the motor and the chamber in a stable relationship, and a means for connecting the motor drive member to the reciprocating means to produce the fluid flow.

The lavage system incorporating the linear motor has been found to be surprisingly effective. In addition to providing a lavage system that produces a strong pulsatile flow the frequency of which is easily controllable, it also enables one to control the volume of flow independently of the frequency without relying on the inefficient throttle method. In addition, it has been found that the system is much quieter than prior art systems, which is very important for hospital use. Surprisingly, all this is possible in a system that is small, rugged, and highly efficient compared to the prior art systems.

Numerous other features, objects and advantages of the invention will now become apparent from the following detailed description when read in conjunction with the accompanying drawings, in which:

BRIEF DESCRIPTION OF THE DRAWINGS

FIG. 5 is a side view of the housing of FIG. 3 showing the preferred pulsatile lavage/irrigation pumping chamber;

FIG. 6 is a side view of the housing showing the suction pumping chamber, and indicating the manner of insertion of the pump;

FIGS. 11A thru 11L show more detailed electrical diagrams of the various portions of the electronics of FIGS. 10A and 10B;

DESCRIPTION OF THE PREFERRED EMBODIMENT

Figure 1:
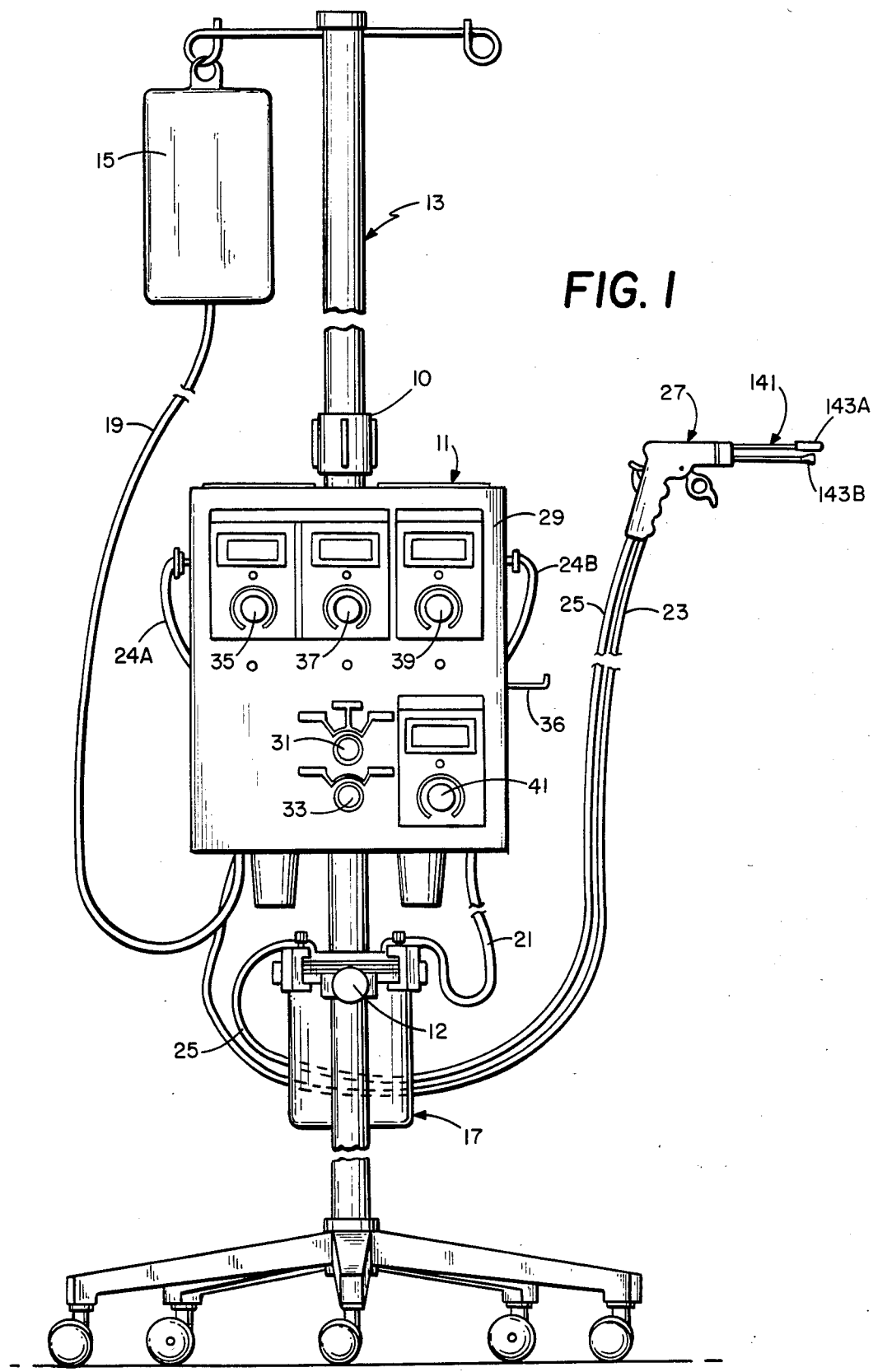
FIG. 1 is a front view of a lavage system in accordance with a preferred embodiment of the invention.
Figure 2:
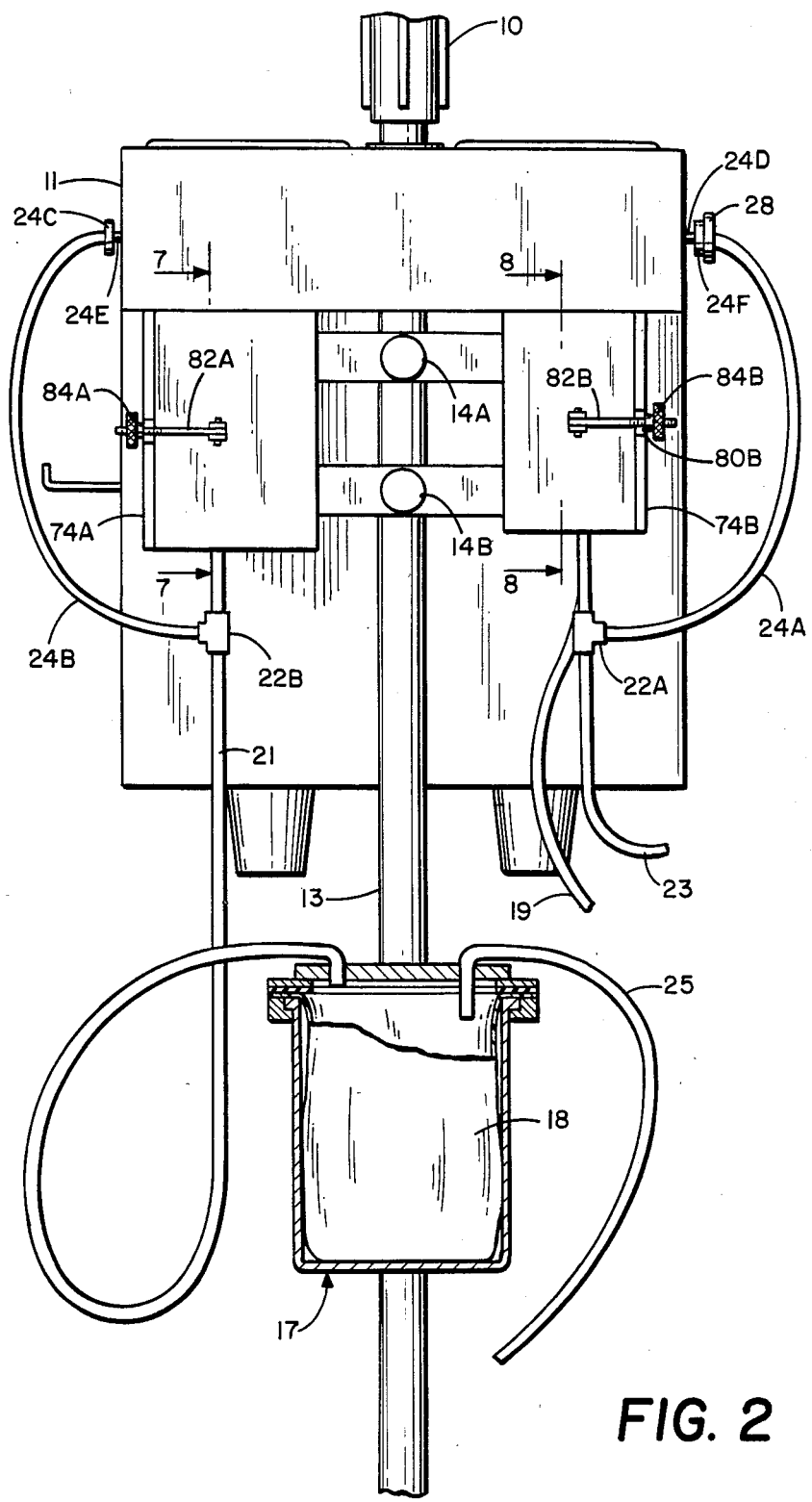
FIG. 2 is a partial rear view of the lavage system of FIG. 1.
Figure 3:
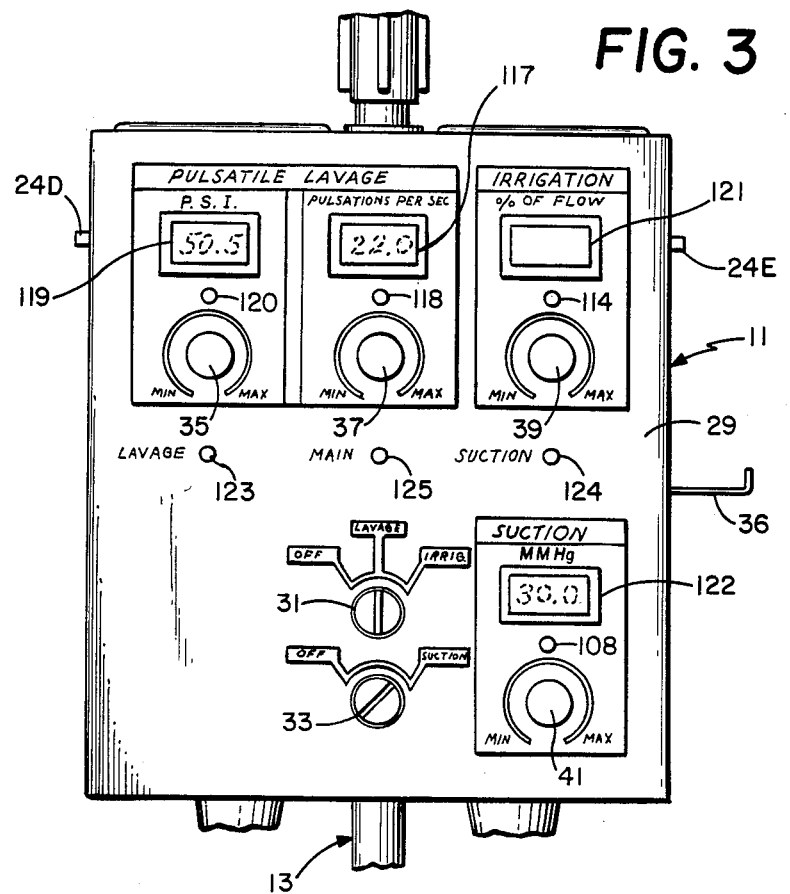
FIG. 3 is a front view of the housing for the lavage system of FIG. 1.

Referring to FIGS. 1-3, external views of the lavage system according to this invention are shown. The system includes a housing 11 mounted on a movable stand 13 along with a supply 15 of fluid such as saline solution. Below the housing 11 and also mounted to the stand 13 is a drainage tank 17. The fluid supply 15 is connected to a pulsatile lavage/irrigation pump 51A (not shown in these FIGS.) in the housing 11 by line 19, and the drainage tank 17 is likewise connected to a suction pump 51B (also not shown) in the housing 11 by line 21. The pumps will be described later. A pulsatile lavage/irrigation fluid line 23 connects the pump 51A to a lavage handpiece 27 to provide a stream of fluid at nozzle 143B. A suction line 25 connects the lavage handpiece 27 to the drainage tank 17. The vacuum line 21, connecting the drainage tank 17 to the suction pump 51B in the housing 11, provides fluid suction at the nozzle 143A via line 25.

The housing 11 contains linear motors, pumps and circuitry which provide pulsatile lavage and irrigation functions by pumping fluid from the supply 15 to the lavage head 27 via line 23 and provide an aspirating function by pumping fluid from the lavage head 27 via line 25 to the drainage tank 17 by providing vacuum at line 21. Hereinafter in this description, for simplicity and to avoid suggesting that there may be more than two motors and pumps, we shall refer to the motor, pump and the associated components which provide both the pulsatile lavage and irrigation functions by the designation PL/IR.

Referring to FIG. 3, the pulsatile lavage, irrigation and suction functions are controlled at control board 29. A pair of switches 31, 33 operate the PL/IR and suction pumps, respectively. The suction control switch 33 is a two-position on/off switch, while the PL/IR control switch 31 is a three-position switch having an "off" position, a "lavage" (here short for pulsatile lavage) position and an "irrigation" position The PL/IR control switch 31 is used to switch the PL/IR motor from "off" to "lavage" and "irrigation" control modes with "lavage" mode control being effected by control knobs 35 and 37 and "irrigation" mode control being effected by knob 39. In this embodiment the suction pump is operable in only a single "suction" mode which is controlled by knob 41.

It can be seen that the system can be controlled in three "on" modes "lavage," "irrigation," and "suction." Further, "lavage" when used in connection with knob 31 is short for the term pulsatile lavage used elsewhere herein. Moreover, both the "lavage" and "irrigation" modes provide irrigation in the sense that they both provide a stream of liquid. Likewise, while in the present embodiment the "lavage" mode does not control suction, suction is generally considered to be an integral part of surgical lavage. For this reason, the choice of terminology chosen to distinguish the three functions of the preferred system should not be considered to be limiting when these terms are used in somewhat different senses in other contexts.

Having provided a brief orientation to the drawings and the functions of the preferred system we shall now return to FIGS. 1 and 2 and proceed with a more detailed description.

Stand 13 includes a collar 10 for adjusting the height of the upper portion, and thus the height of fluid supply, above the housing 11. Housing 11 includes knobbed set screws 14A and 14B for adjusting its height on stand 13. Drainage tank 17 also includes a knobbed set screw 12 for adjustment of its height.

We have already described the connection of tubes 19, 21, 23, and 25. The system also includes tubes 24A and 24B. One end of line 24A connects to "T" 22A in line 23 and the other end connects to the pressure transducer coupling 24D. The connection is made by means of a leur lock connector 24F having a filter 28 attached to prevent contamination of the fluid in tube 23 by transducer 26A (FIG. 5). One end of line 24B connects to "T" 22B in line 21 and the other end connects to suction transducer coupling 24E via leur lock connector 24C. The transducers 26A and 26B will be discussed in more detail in connection with FIG. 9. Also shown in FIG. 2 is a disposable drainage bag 18 which optionally fits within tank 17. In another embodiment bag 18 may be replaced by a disposable rigid canister.

Figure 4:
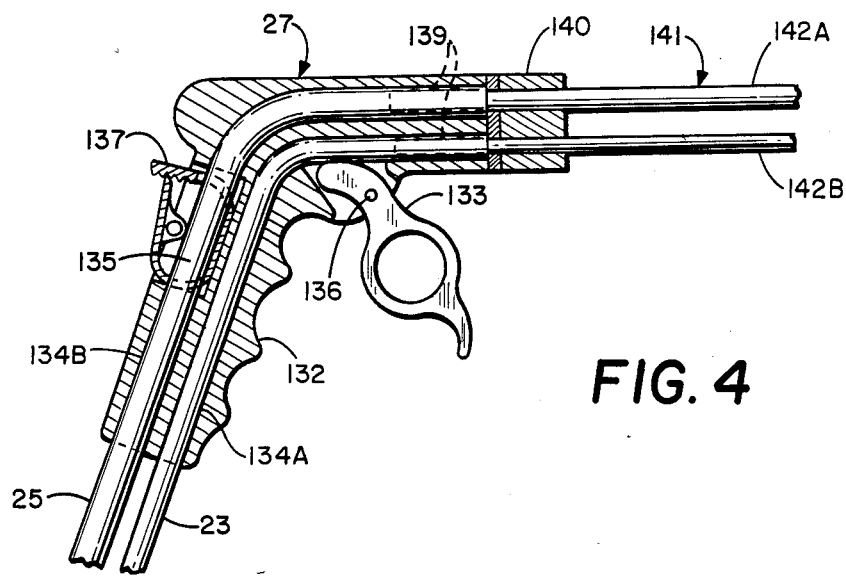
FIG. 4 is a sectional view of the lavage handpiece.

Referring to FIG. 4, the lavage handpiece 27 in the preferred embodiment includes a pistol-shaped body 132 and a pair of pinch valves 133 and 135, which are secured in hollows molded in body 132. A pair of cylindrical channels 134A and 134B are formed within body 132 of an appropriate size to accept the ends of tubing 23 and 25. Pinch valve 133 is rotatable about pin 136 to pinch off tubing 23. Serrated arm 137 holds pinch valve 135 in an open or closed position. It is made of a flexible material so that it may be raised upward to release pinch valve 135 as desired. Attached to the lavage handpiece 27 is a nozzle tube assembly 141 which comprises two semi-rigid tubes 142A and 142B held in a plug 140, and a pair of nozzles 143A and 143B (FIG. 1) attached to the ends of tubes 142A and 142B respectively. The proximal ends of tubes 142A and 142B fit into the open ends 139 of tubes 23 and 25. In the preferred embodiment these nozzles and tubes form a replaceable assembly which is described in detail in a companion application. Since the particular form of the nozzles are not a part of this invention they will not be discussed further herein.

Referring to FIGS. 5-8, the pulsatile lavage/irrigation pump 51A and suction pump 51B are shown. Each pump 51A and 51B is attached to an electric driving motor, which according to the invention is a linear motor; however, only one motor 53 is shown (attached to pump 51B) as the other motor is identical. Each motor, such as 53, is connected to its pump, such as 51B, by a coupling 59. Each coupling 59 consists of a pin 61 and a pair of flange sections 63, 65 associated with the motors 53 and pumps (51A or 51B) respectively. Each pin 61 is located on the motor flange 63 and inserts into a hole 57 in the pump flange 65. Each flange 65 is connected to a piston rod which is the driven member of the pump; piston rod 67A in the case of pump 51A and piston rod 67B in the case of pump 51B.

Figure 7:
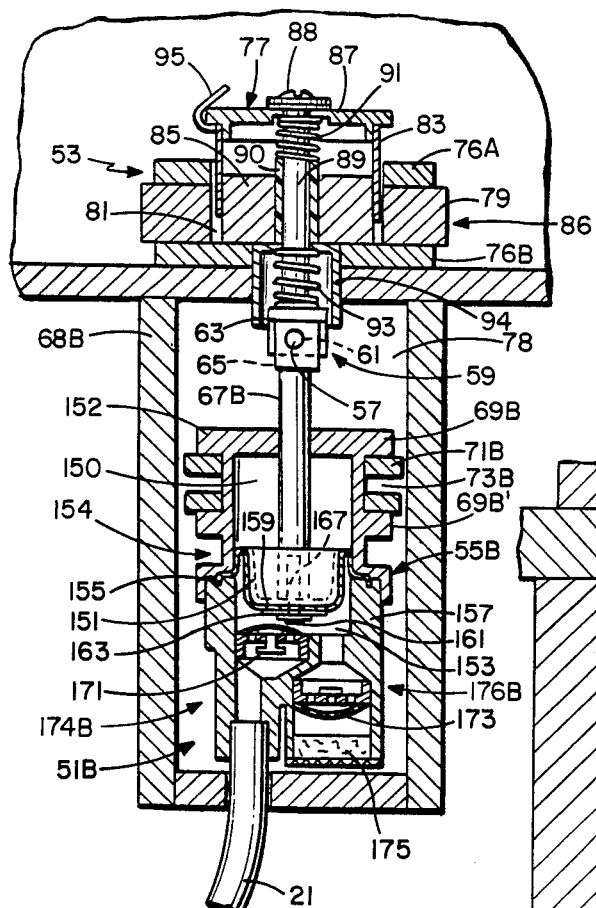
FIG. 7 is a (cut-away) sectional view taken along line 7—7 of FIG. 2, showing the preferred suction pumping chamber and an embodiment of a moving coil linear motor according to the invention.

Referring to FIG. 7, and in particular, the lower portion of the figure, the suction pump 51B is shown. The pump includes a pump body 55B having an upper portion 152 and a lower portion 157 which enclose a cylindrical chamber 154, which chamber is divided into a upper portion 150 and a lower portion 153 by a diaphragm 151. Diaphragm 151 includes an outer lip 155 which is secured between the two housing portions 152 and 157. The center part of diaphragm 151 is sandwiched between a cup 159 and washer 163 and the assembly is secured to shaft 67B by a screw 161 which screws into a threaded hole 167 in the end of rod 67B. Inlet umbrella valve 171 and outlet umbrella valve 173 seat in inlet and outlet ports 174 176B, respectively of chamber 154. Filter 175 seats in the lower portion of the outlet port 176B.

Figure 8:
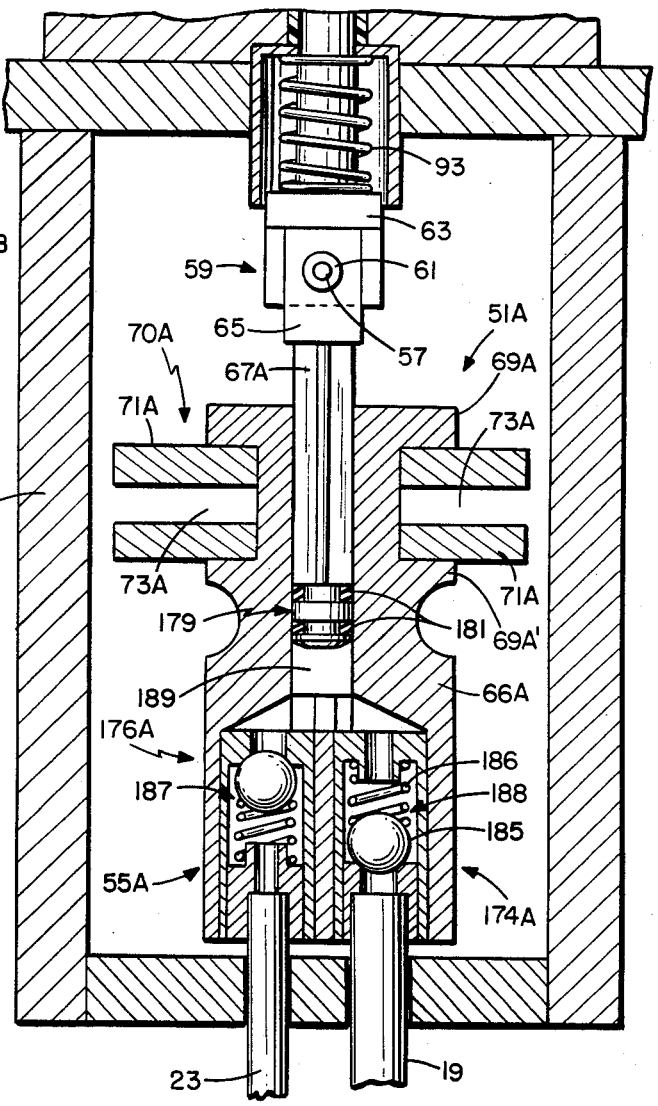
FIG. 8 is a (cut-away) sectional view taken along line 8—8 of FIG. 2, showing the pulsatile lavage/irrigation pumping chamber used in the invention.

Referring to FIG. 8, the PL/IR pump 51A is built somewhat differently than the suction pump because of its different function. The molded pumping housing 66A encloses a cylindrical chamber 189 which is sealed by plunger 179, which is comprised of two O-rings 181 which fit into grooves in the end of rod 67A. The outlet and inlet valves 187 and 188 respectively are ball valves comprised of resilient balls such as 185 which are normally held in the closed position by springs 186.

Referring to FIG. 6, the apparatus for holding a pump within the housing 11 shall be described in reference to the suction pump 51B. An upper pair of flanges 69B and a lower pair of flanges 69B′ extend from the pumping chamber housing 66B. Within suction pump enclosure 68B is a suction pump support 70B which is shaped somewhat like a four-finger tuning fork having fingers 71B. Pump 51B fits into enclosure 68B with flanges 69 passing above the upper pair of fingers 71B and flanges 69B passing below the lower pair of fingers 71B. A backing plate 78 (not shown in FIG. 6) is located so that pump 51B slides up against it when pin 61 has fully entered the hole 57 in flange 65 and flange 65 and 63 engage. Door 74B mounted on enclosure 68B may then be closed. When door 74B is closed, wedges 75B located on door 74B slip in between the fingers 71B forcing them apart and causing them to firmly engage flanges 69B and 69B′ on pump 51B, thus holding pump 51B firmly in place. Rod 82B is then pivoted into slot 80B in door 74B and locking nut 84B is screwed inward to secure the door (this is perhaps best seen in FIG. 2). Referring to FIG. 5, pump 51A is likewise secured in enclosure 68A by slipping flanges 69A and 69A′ about fingers 71A and, closing door 74A so that wedges 75A force fingers 71A open, slipping rod 82A into slot 80A and screwing nut 84A tight to secure the door.

Referring to FIG. 7, the motor 53, in the embodiment shown, is a moving coil linear reciprocating motor. It comprises a coil 83 and a core 86. Coil 83 is fixed to drive member 77 of motor 53. Core 86 comprises an outer permanent magnet portion 79 and an inner non-magnetized but magnetically permeable portion 85. A cylindrical slot 81 is formed within core 86, and coil 83 moves within this slot. Magnetically permeable steel plates 76A and 76B sandwich the permanent magnet, and also may be considered as part of the motor core. Drive member 77 comprises connecting member 87 and shaft 89. Connecting member 87 is in the form of a circular plate. Plate 87 is attached to shaft 89 by screw 88. A hollow cylindrical bearing 90 fits into a cylindrical bore in core 86 and shaft 89 slides within bearing 90.

The portion of shaft 89 that slides in bearing 90 is a journal. A variable damping means comprising helical coil spring 91 is located on shaft 89 with the axis of the spring corresponding to the axis of the shaft, and with one end of the spring seating against plate 87 and the other end of the spring seated against bushing 90. Similarly the coil spring 93 fits coaxially about the bottom of the shaft 89 and seats between the top of flange 63 and a spring enclosure 94 which forms an integral part of bushing 90. It is noted that the springs 91 and 93 will function properly as long as one end is seated against a portion of the motor that is moveable with the coil while the other end is seated against a portion of the motor which is fixed to the core. Thus, in the context of providing a seat for the spring, bushing 90 may in this embodiment be considered to be part of the motor core. Coil 83 is electrically connected to circuitry in the housing by means of braided wires 95. It is noted that the housing 68B, including fingers 71B is a means for supporting the motor 53 and pump body 55B in a stable relationship, so that the motor can drive reciprocating means 67B in the pump chamber 150, 153.

Figure 12:
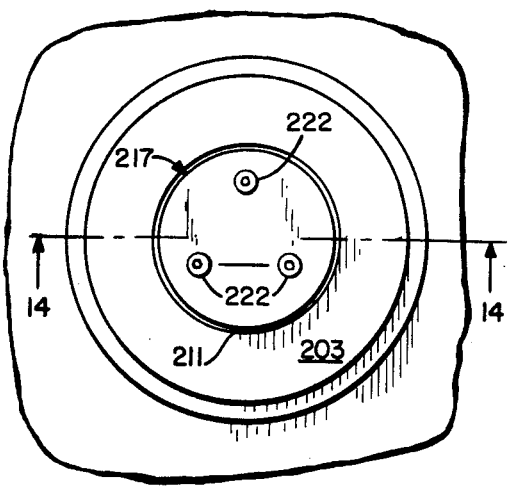
FIG. 12 is a top view of the preferred moving coil linear motor according to the invention.
Figure 13:
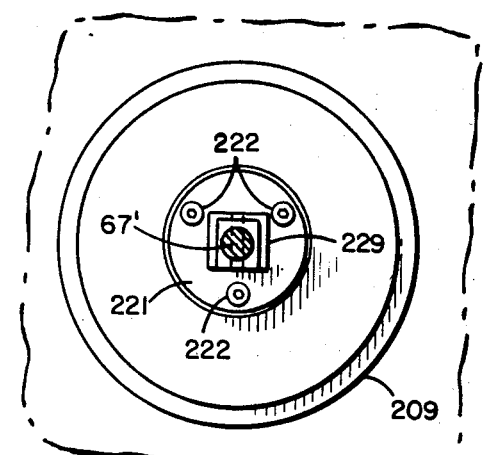
FIG. 13 is a bottom view of the motor of FIG. 12.
Figure 14:
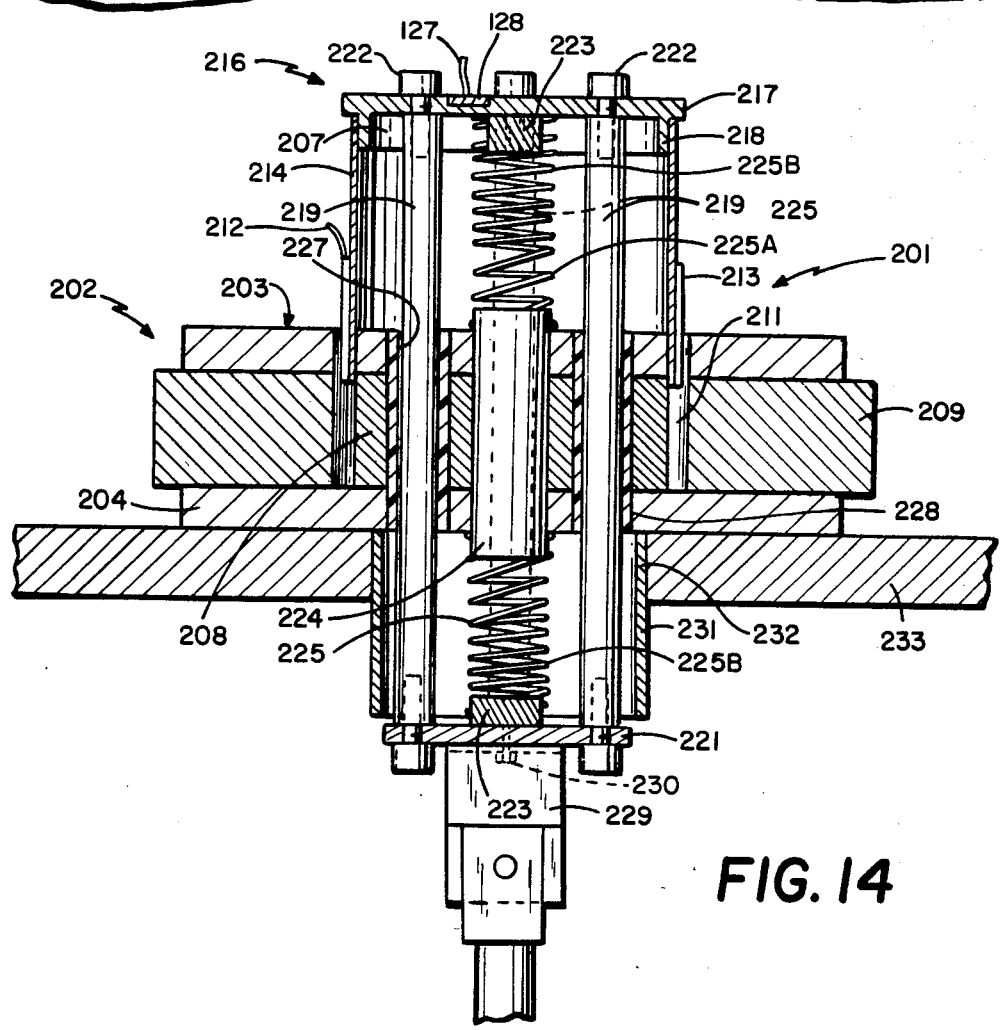
FIG. 14 is a cross-sectional view of the motor of FIG. 12, taken along lines 14—14.

Referring to FIGS. 12, 13, and 14 an alternative embodiment of the linear motor is shown. This embodiment is presently the preferred embodiment. A top view of the motor is shown in FIG. 12, a bottom view in FIG. 13, and a cross-sectional view in FIG. 14. Motor 201 comprises a core 202, a moving coil 213, and a drive member 216. Core 202 includes a magnetically permeable top plate 203, a magnetically permeable bottom plate 204, an inner magnetically permeable core 208 and a permanent magnet 209. Coil 213 moves in a cylindrical slot 211 between magnet 209 and inner core 208. Drive member 216 comprises coil support 214, a pair of connecting members 217 and 221 in the form of circular plates, shafts 219, and screws 222. Coil 213 is attached to cylindrical coil support 214 which in turn is attached to a ring-shaped flange extending from the bottom of upper connecting plate 217. Upper plate 217 is secured to lower plate 221 by the three shafts 219 by means of screws such as 222. Shafts 219 are moveable in bearings 227 which seat in cylindrical bores 228 through core 202. Variable damping means comprising coil springs 225 seat between the core 202 and connecting plates 217 and 221. Spring alignment bosses 223 are attached to the center of connecting plates 217 and 221 and spring alignment post 224 seats in a cylindrical bore through the center of core 202. One end of the spring 225 fits around the bosses 223 and the other end fits around the post 224 to maintain the spring in alignment. Springs 225 are helical coil springs with varying coil spacing; that is, the coil spacing at one portion 225A of each spring 225 is different than the coil spacing at another portion 225B of the same spring 225. The spacing is chosen so that the motor 201 will have biasing force toward the center position which varies along the excursion path of the drive section 216 in a predetermined manner. The motor is attached to flange 229 by screw 230, and the rest of the attachment to the pump is as described above. The motor 201 sits in a cylindrical hole 232 in pump housing 233. A thermistor, such as 128, is encapsulated in epoxy and bolted to the top plate 217 and is connected to the electronic circuitry, which shall be described below, by braided wires 127. Coil 213 is connected to the electronic circuitry by braided wires 212.

Figure 9:
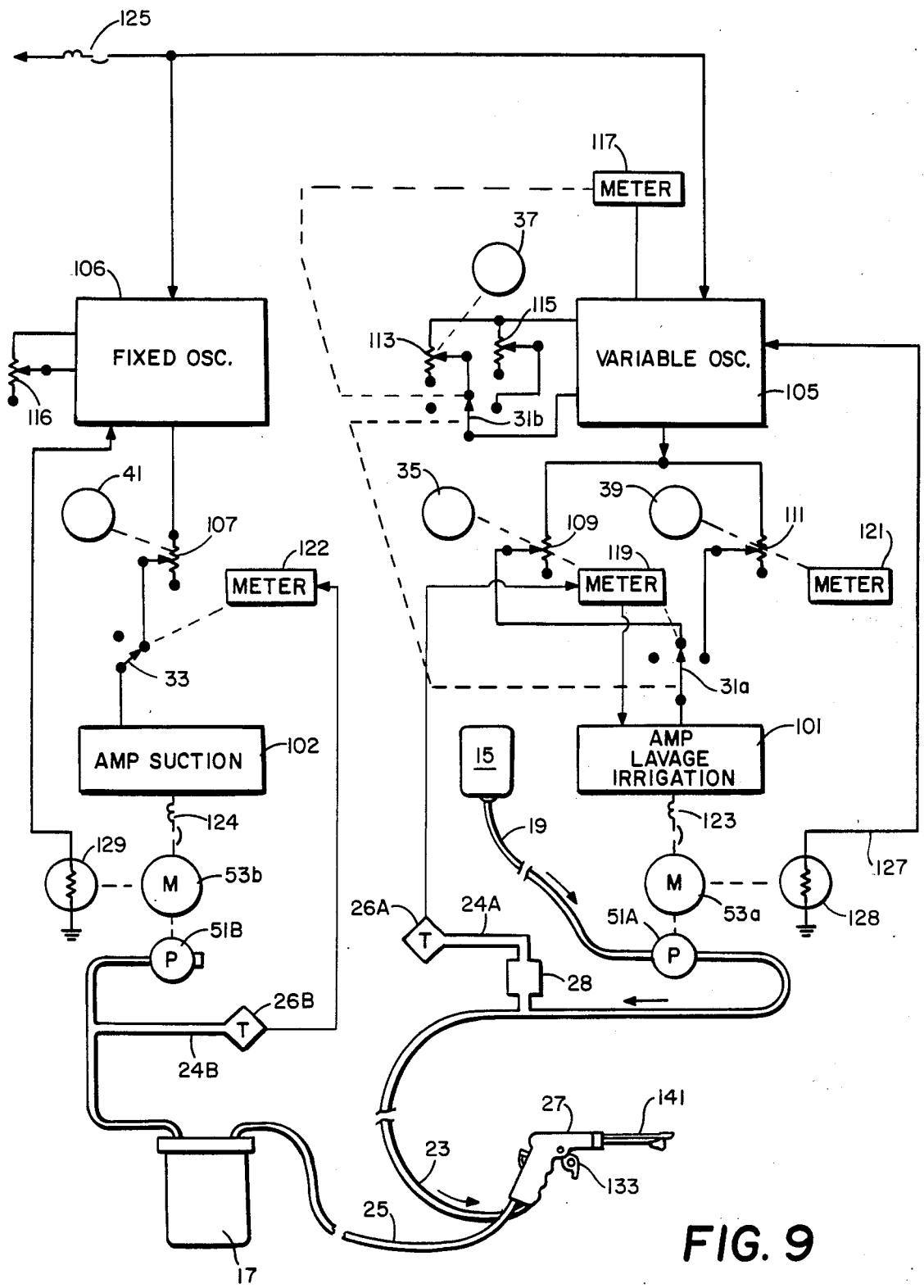
FIG. 9 is a block diagram showing the operation of the controls and various functions of the preferred embodiment of the invention.

Referring to FIG. 9, a discussion of the electrical circuitry in terms of a functional diagram will be given before proceeding to the detailed discussion of the circuitry, in order to make that discussion more clear. In FIG. 9 the physical connection between pump 51A and motor 53a and pump 51B and motor 53b is shown by a dotted line. Power for the motors 53a and 53b is supplied by a signal provided by amps 101 and 102 respectively which is applied to the motors through circuit breakers 123 and 124 respectively. Oscillating signals which are amplified by amplifiers 101 and 102 are provided by oscillators 105 and 106 respectively. Power to the oscillators is provided through circuit breaker 125.

The switches in FIG. 9 correspond to the switches in FIG. 3. These switches are actually double pole switches. The two poles of switch 31 are shown separately at 31a and 31b in FIG. 9 for clarity. The dotted line indicates that the two switches move together.

As can be seen in FIG. 9, switch 33 has a closed position in which it connects the fixed oscillator 106 to the suction amplifier 102, which is the suction "on" position, and an open circuit position which is the suction "off" position. In the "on" position switch 33 also activates meter 122 to read the vacuum from the suction transducer 26B. This is shown by the dotted line. Meter 122 could also be connected to read the power going through variable resistor 107, or the power off the amplifier 102, both of which would give a meaningful output to the meter.

The far left position of switches 31a and 31b is an open circuit "off" position. In the central position switch 31a connects variable resistor 109 which is controlled by knob 35 into the circuit between oscillator 105 and amp 101. Variable resistor 109 controls the amplitude of the signal to amplifier 101 and thus controls the power output of the amplifier and ultimately of the pump. Since the power output of the pump is directly related to either the rate of flow or the pressure, meter 119 can be calibrated in either percent of power units, pressure units, or rate of flow units. In the embodiment described, it is chosen to calibrate the meter in pressure units, and the pressure is read off pressure transducer 26A by meter 119 when switch 31a is in the central position. The pressure units chosen are pounds per square inch. Of course, any other pressure units, such as millimeters of mercury could also be chosen. In the central position, switch 31b connects variable resistance 113 into the variable oscillator 105 circuitry. Variable resistance 113 is controlled by knob 37, the pulsatile lavage frequency control, to control the frequency of variable oscillator 105. In the central position switch 31b also connects meter 117 to the circuitry of variable oscillator 105. In this position of switch 31b, meter 117 displays the frequency of oscillation of the variable oscillator 105. In the far right position switch 31a connects variable resistance 111 between oscillator 105 and amplifier 101. Variable resistance 111 is controlled by knob 39 which, as can be seen from FIG. 3, is the irrigation power control. Meter 121 displays the output of variable resistance 111. Again this output can be calibrated in either pressure units, rate of flow units, or a power unit. In the present embodiment it is chosen to calibrate it in percent of flow. In the far right position, switch 31b connects variable resistor 115 into the electrical circuit of variable oscillator 105. Variable resistance 115 is not controlled by an external knob, but rather is controlled by a "behind the set" control which determines the "fixed" frequency of the irrigation mode. Generally this resistance is set so that a high oscillation frequency, i.e. in the range between 30 and 40 cycles per second is chosen since a high frequency provides a nearly continuous flow. In the embodiment shown switch 31b when switched to the far right position deactivates the meter 117, although one obviously could choose to leave the meter connected in this situation if one desired to read out the "fixed" frequency.

The oscillation frequency of fixed oscillator 106 is determined by variable resistance 116, which is also a "behind the set" control. The setting of variable resistance 116 determines the frequency of the suction motor and pump.

Also shown in FIG. 9 are thermistors 128 and 129 which are physically attached to motors 53a and 53b as shown by the dotted lines. Thermistors 128 and 129 are temperature sensitive resistors which in a voltage divider circuit will vary the voltage output of the circuit proportionally to the temperature of the motor. As the temperature of the motor increases the internal resistance of the moveable coil increases which reduces the effective power produced by the motor. The output of the voltage divider circuit incorporating thermistors 128 and 129 is fed into the circuitry of the oscillators 105 and 106 respectively. The circuitry is arranged so that this output causes the power input to the oscillators 105 and 106 respectively, and therefore the power level of the oscillator output signal to increase precisely as needed to account for the variation of performance of motors 53a and 53b respectively with temperature.

FIG. 9 also shows a connection between pressure transducer 26A and amplifier 201 through meter 119. By means of this connection, the circuitry causes the amplifier 101 to shut down if the pressure in line 23 rises above a certain predetermined pressure, and to turn back on when the pressure drops below that predetermined pressure. This circuitry causes motor 53a and pump 51A to shut down whenever valve 133 on the lavage handpiece (FIG. 4) is closed, and to resume operation when the valve 133 is opened.

Figure 10A:
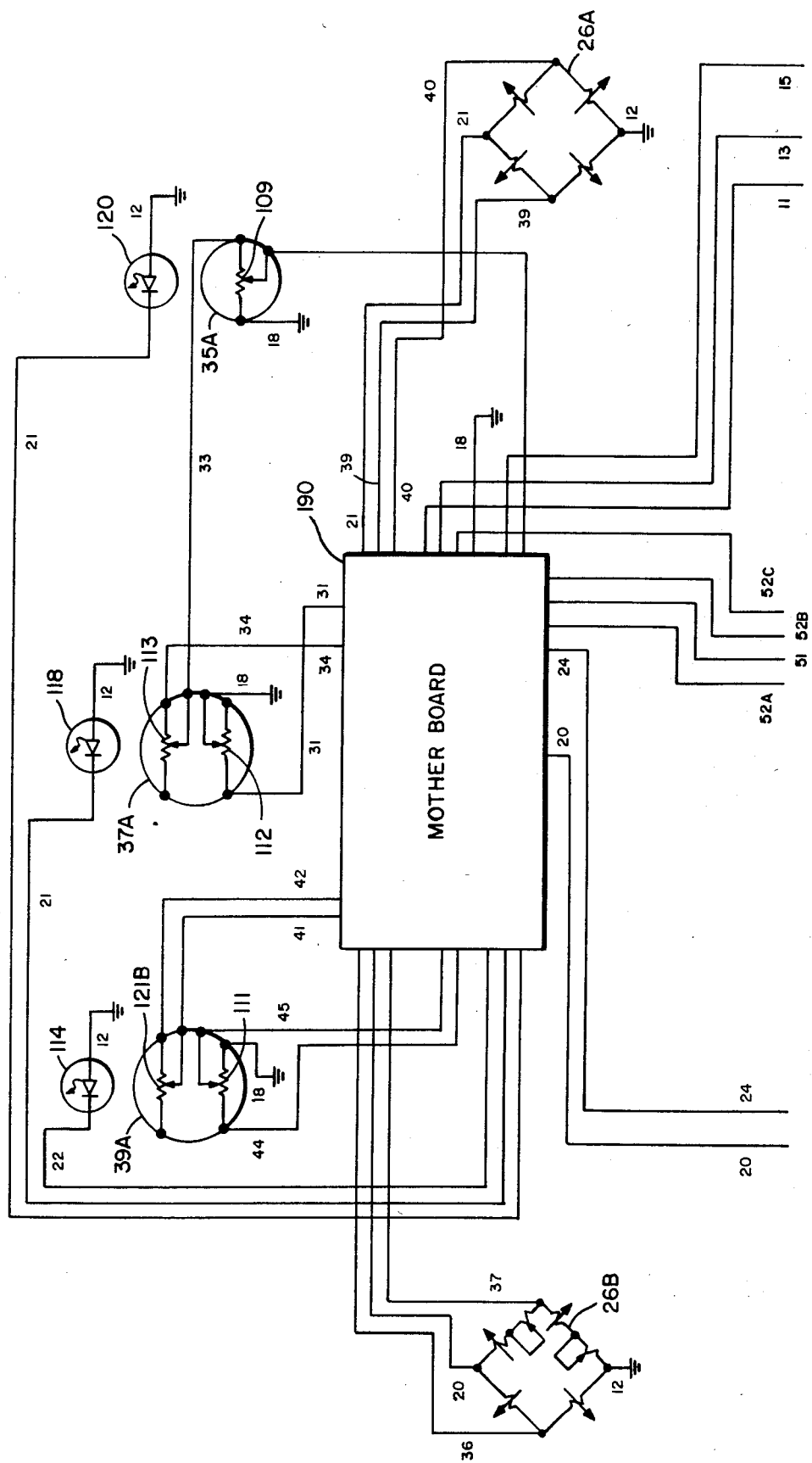
FIG. 10A is the upper half and FIG. 10B is the lower half of a schematic diagram of the electronics according to the preferred embodiment of the invention.
Figure 10B:
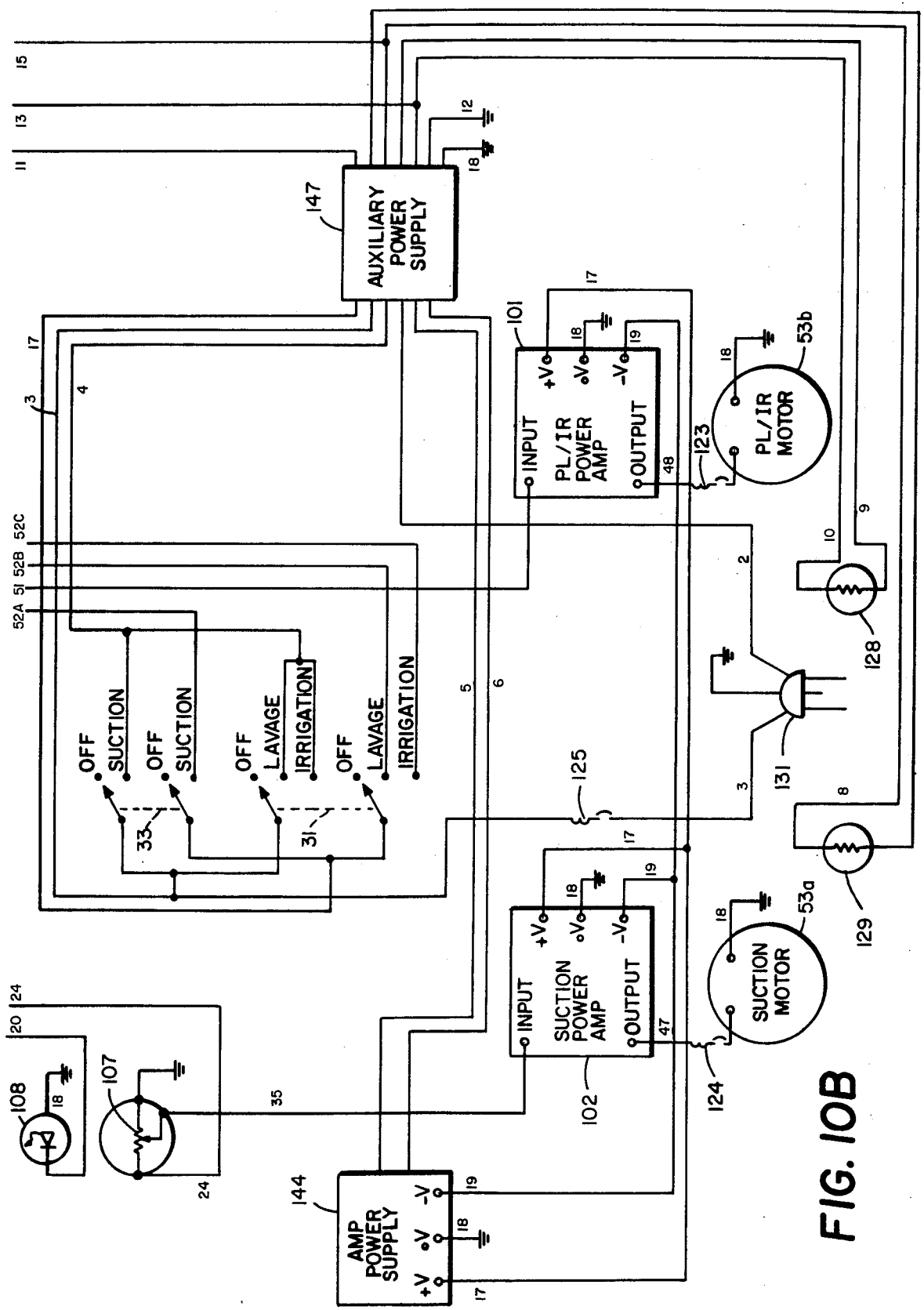

Turning now to a more detailed description of the electronic circuitry, the electrical interconnections of the various electronic components is shown in FIGS. 10A and 10B. If FIG. 10A is placed above FIG. 10B, so that the wires leaving FIG. 10A at the bottom of the page overlap the wires entering FIG. 10B at the top of the page, a complete electrical schematic of the electronic portion of the invention is obtained. The numbers contained in small circle in FIG. 10A and 10B label the individual wires, and thus enable the wires to be traced from one page of the drawing to the next. Note that some wires carry identical numbers, for example 21 and 18. This is an indication that these wires connect at some point, usually on the Motherboard. Beginning at the top of FIG. 10A and proceeding to the bottom of FIG. 10B, the components of the electrical circuit include light emitting diodes (LED) 114, 118, and 120 which are illuminated as appropriate to show that the irrigation function, the pulsatile lavage frequency control function, and the pulsatile lavage pressure control function respectively are operating (see FIG. 3). Beneath these diodes are two dual potentiometers 37A and 39A and a single potentiometer 35A which contain the variable resistors 109, 111, and 113, which function as described above in connection with FIG. 9. Potentiometers 35A, 37A, and 39A are controlled by knobs 35, 37, and 39 respectively (see FIGS. 3 and 9). Variable resistor 121B in dual pot 39A is part of the circuit regulating irrigation meter 121 to provide the proper meter output. Variable resistor 112 in dual pot 37A provides an adjustment to the gain of amplifier 101 to keep the amplifier output flat as the frequency changes. Beneath the dual pots are the irrigation/lavage transducer 26A and the suction transducer 26B, also described in FIG. 9, and the Motherboard 190. Motherboard 190 is hybrid circuit which provides for most of the connections between the various electrical components, and which shall be described below in connection with FIGS. 11A through 11L. At the top left of FIG. 10B is suction LED 108 (See FIG. 3) and the suction amplifier potentiometer 107 which functions as described in reference to FIG. 9. Switches 31 and 33 connect power socket 131 with the power supplies and the Motherboard through circuit breaker 125. The amplifier power supply 144 supplies power to the amplifiers 101 and 102, while the auxiliary power supply 147 supplies power to the other components in the circuit. Amplifier 101 is connected to PL/IR motor 53a through circuit breaker 123 while amplifier 102 is connected to suction motor 53b through circuit breaker 124 as discussed in reference to FIG. 9. The thermistors 128 and 129, which are mounted on the PL/IR motor 53a and the suction motor 53b respectively, are connected with the auxiliary power supply and the Motherboard as indicated.

Figure 11A:
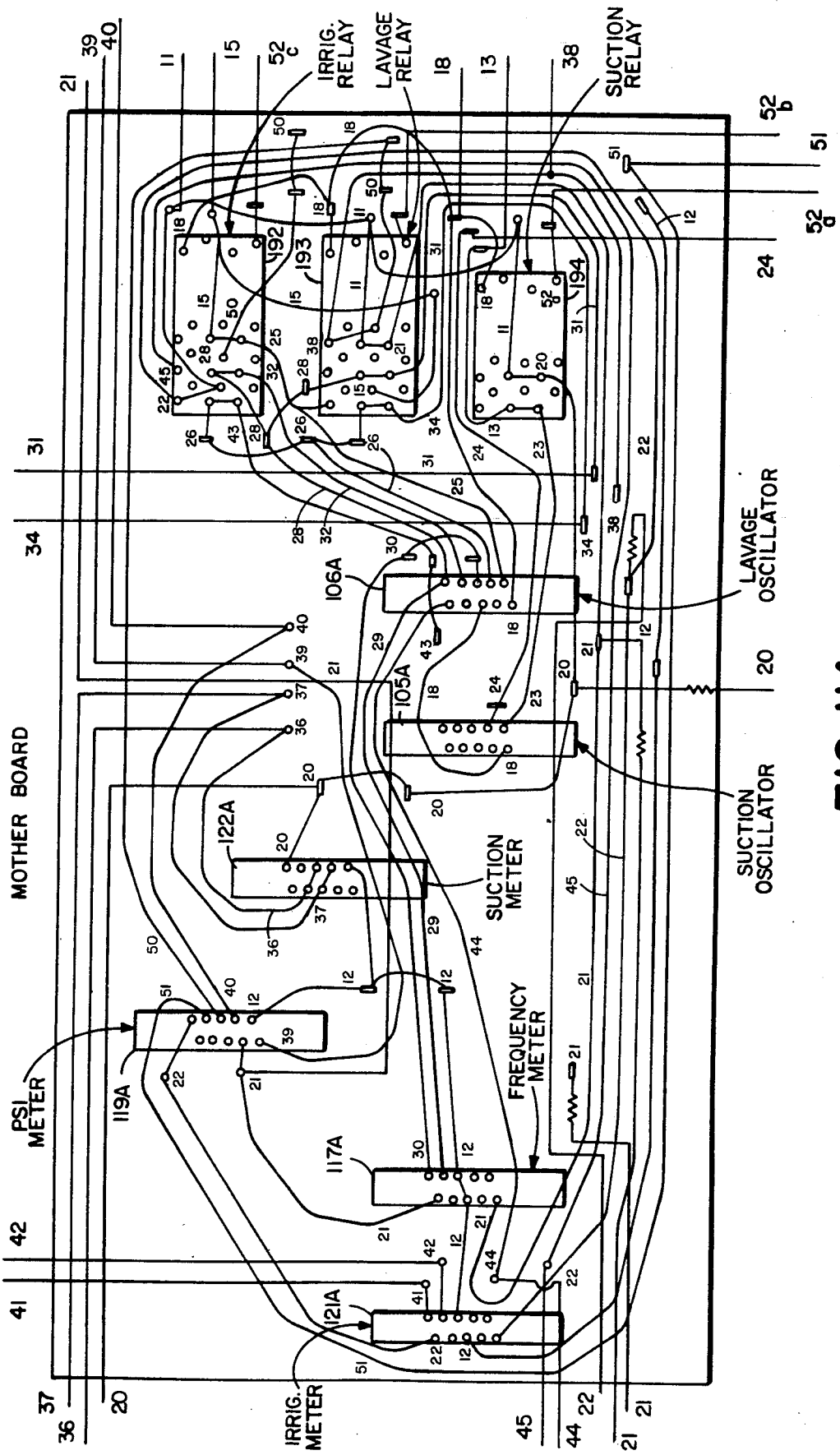
Figure 11B:
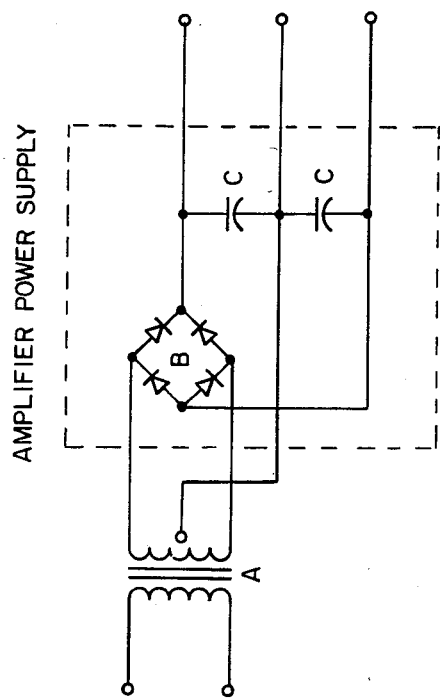
Figure 11D:
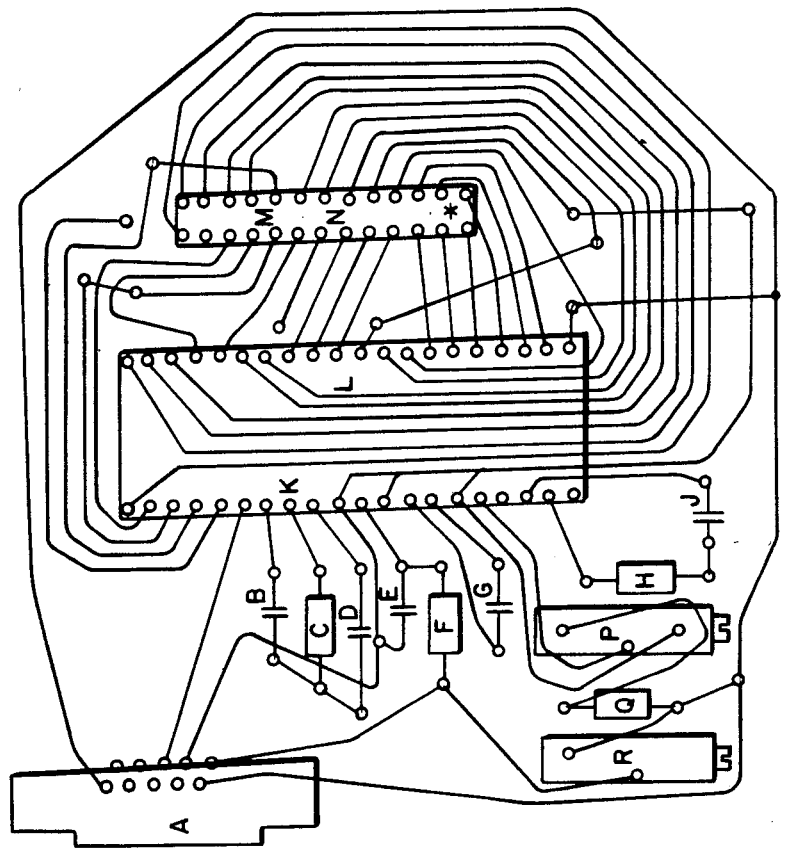
Figure 11E:
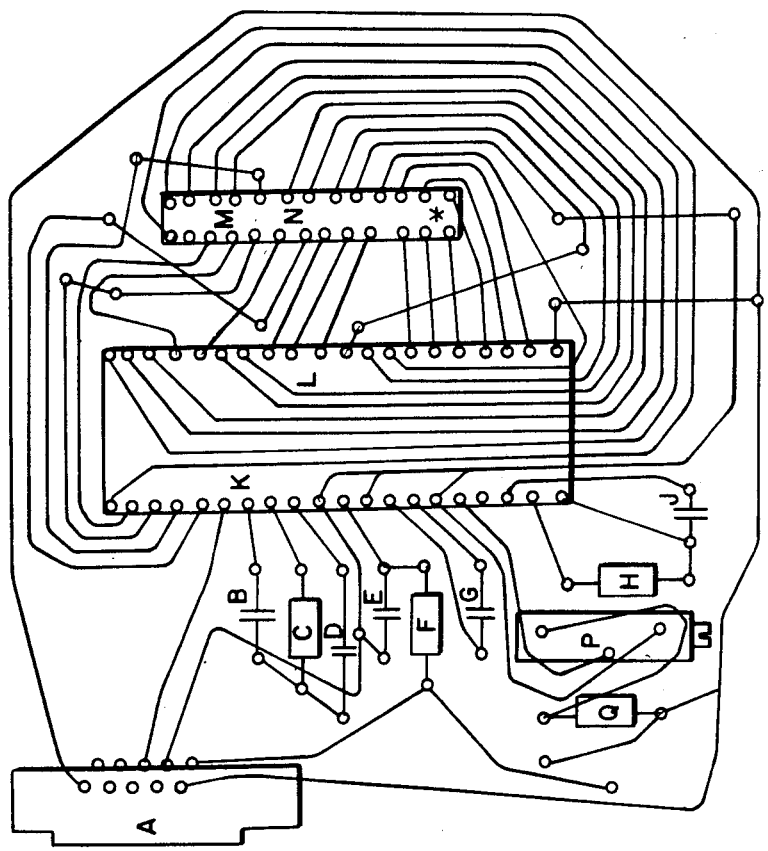
Figure 11F:
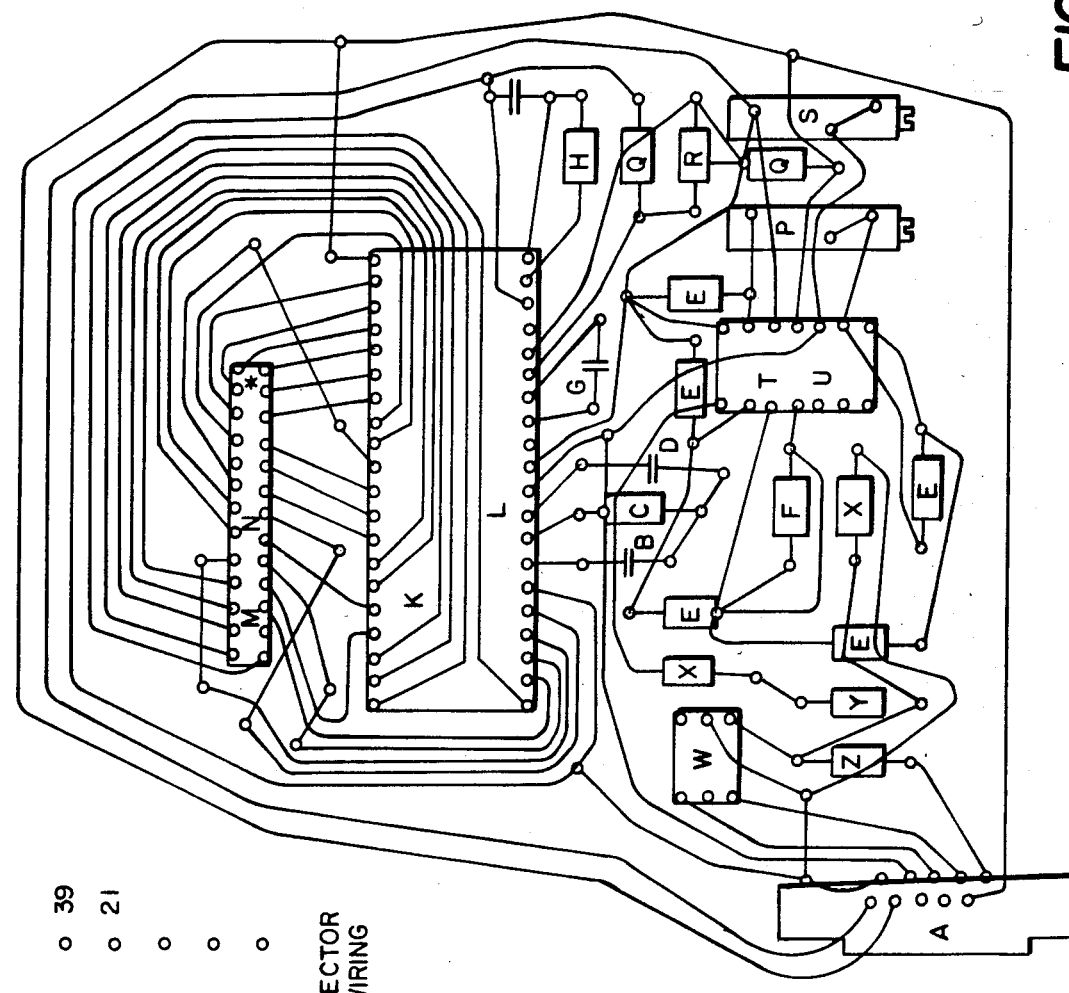
Figure 11G:
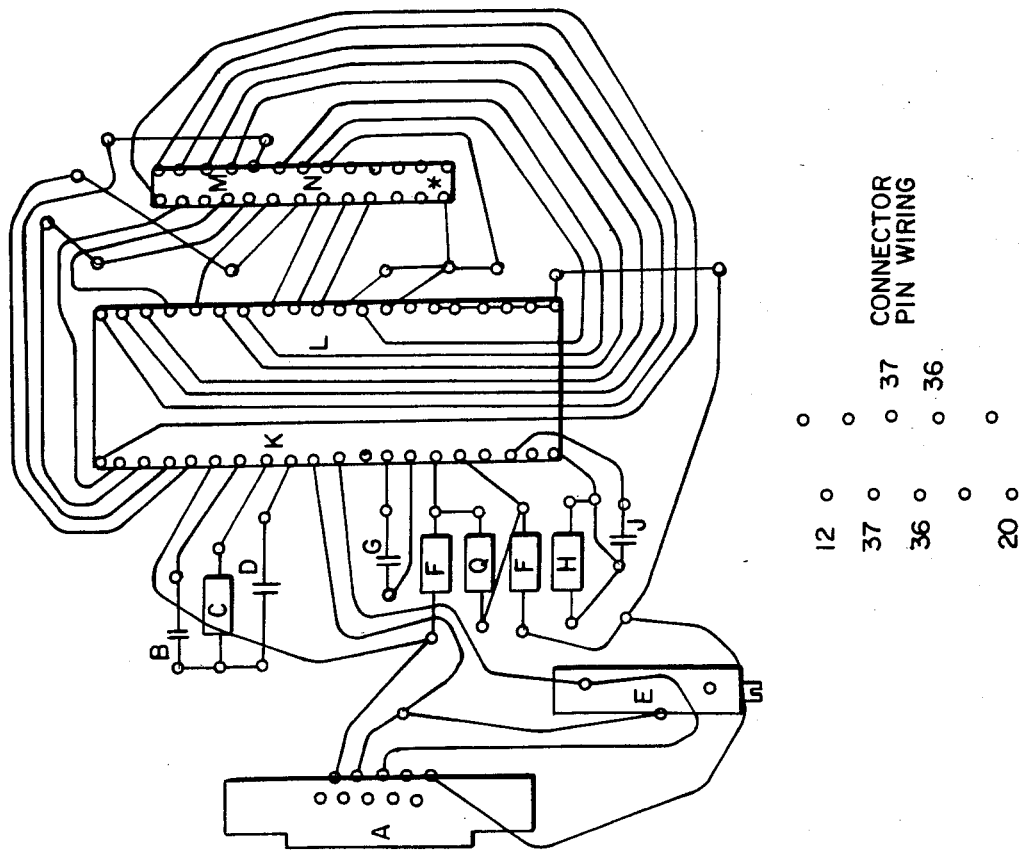
Figure 11H:
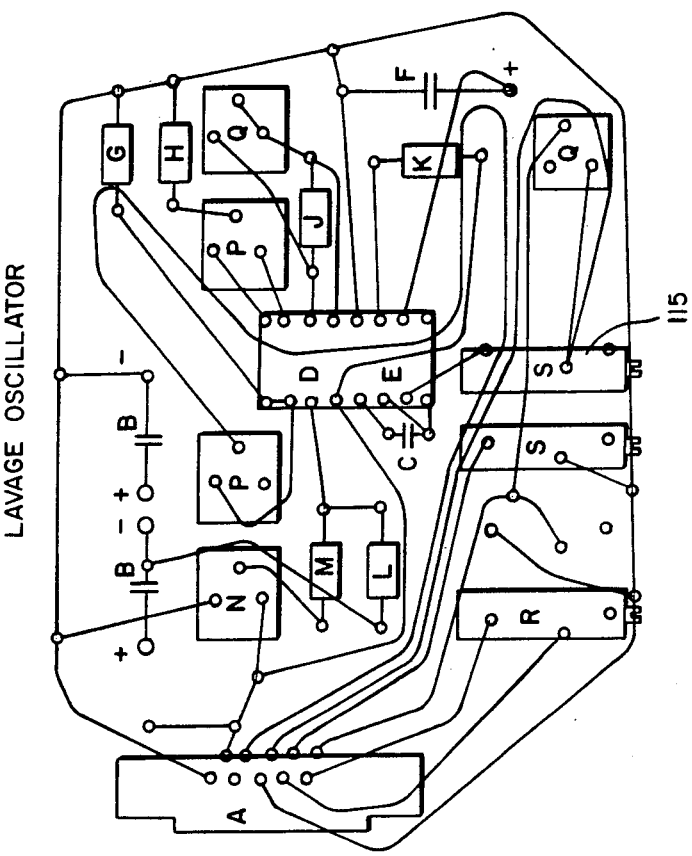
Figure 111:
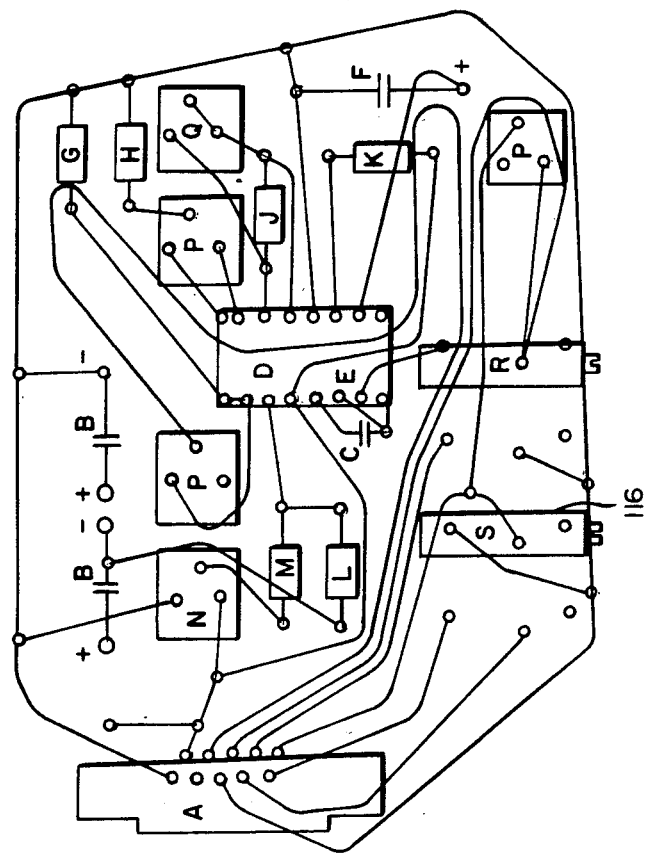
Figure 11L:
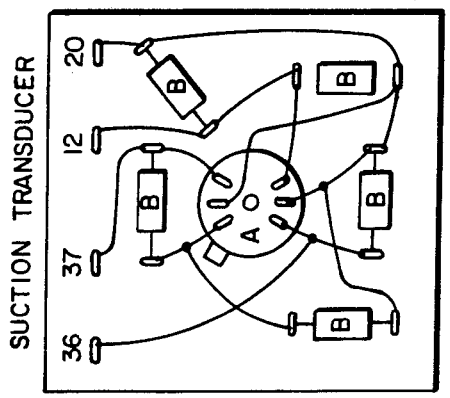

The Motherboard layout is shown in FIG. 11A. The Motherboard includes six subsidiary boards: irrigation meter board 121A, frequency meter board 117A, PSI meter board 119A, suction meter board 122A, lavage oscillator board 105A, and suction oscillator board 106A (see also FIG. 9). The details of each of these boards is given in a subsequent figure. The Motherboard also includes three relays, the irrigation relay 192, the lavage relay 193, and the suction relay 194. The numbered wires shown coming into the Motherboard from outside the figure are the numbered wires entering the Motherboard in FIG. 10A and connecting to the various components shown in FIGS. 10A and 10B. Each of these connections can easily be traced from figure to figure using the numbered wires. The wires connecting the various components on the Motherboard are also labeled with numbers within circles. These wires will be indicated on the detailed drawings of the component boards so that the interconnections will be clear. The ten heavy dots on each of the subsidiary boards are connector pins of WTB10PR7JTA connectors on each of the boards. The pin wiring to these connectors is shown in detail on the subsequent figures. The connections between the subboards and the relays can easily be traced on the Motherboard using the numbered wires, and thus they shall not be discussed further.

The detailed electrical components and connections between the components for the amplifier power supply 144, the auxiliary power supply 147, the irrigation meter board 121A, the frequency meter board 117A, the PSI meter board 119A, the suction meter board 122A, the lavage/irrigation oscillator board 105A, the suction oscillator board 106A, and the suction transducer 26B, are shown in FIGS. 11B through 11I and 11L respectively. Each of these amplifiers, meters, oscillators and transducers are devices that are well understood in the electrical art, which one skilled in the art can build once their function has been described. Instructions on the detailed connections, can usually be obtained with the purchase of the principal parts, and/or will generally be understood from the electrical literature. However, for completeness, each of the individual components is labeled and indicated on the drawings and each of the connections between the components are shown. In each of the drawings the circled numbers represent connections to wires coming into or located on the Motherboard. In each of the drawings which incorporates a WTB10PR7JTA connector, the wiring to the cable connector which presses into the WTB10PR7JTA connector is shown on the drawing. The wiring is shown as it would appear if one turned the cable connector so that the pins are visible and looked down at the pins, since this is the manner in which the cable connector is ordinarily viewed. In each of the drawings the position of the cable locator is shown by a star. The pressure feed back loop which is shown by the connection between transducer 26A and amplifier 101 in FIG. 9 is located on the PSI meter board (FIG. 11F) and consists of the ECG987 quad operational amplifier and the ECG3047 triac opto coupler. These are off-the-shelf items, and instructions for use of the items to produce a feed-back loop may be obtained with purchase of the items The connections to produce the feed-back loop are, of course, also shown in FIG. 11F. The "behind the set" variable resistor 115 for setting the "fixed" irrigation frequency (see discussion of FIG. 9 above) is indicated on FIG. 11H, while the variable resistor 116 for setting the frequency of the fixed or suction oscillator 106 is indicated on FIG. 11I. It may be noticed that while the suction oscillator board (FIG. 11I) shows wires to nine sockets on the connector A, the connector pin wiring on the same figure shows connections to only three pins. This is due to the fact that the suction and lavage oscillator boards are wired the same for manufacturing convenience, but only three pins need to be connected to the Motherboard 190 for the suction oscillator to operate properly.

Each of the meter boards shown in FIGS. 11B through 11G is connected to a liquid crystal display (LCD) to produce the visible meter readings as shown for example on meters 117 and 119 in FIG. 3. The connections between each of the meter boards and its LCD display are identical and are shown in FIGS. 11J1, 11J2, 11K1, 11K2, and 11K3. FIG. 10J1 shows the connection between the component side of the meter board and the back of the LCD board. The connection is made between the 26 pin header 196A (labeled M on each of the meter boards) and a corresponding 26 pin header 196B on the LCD board by means of 26 line cable 197. The location of the 1CL7106CH chip is shown at 198 on the meter board in order to more clearly define the location of the header 196A. The front of the LCD board is shown in FIG. 10J2 and consists of LCD chip 199 mounted on a 40 pin chain terminal 195. The connections between the 26 pin header 196B and the back of the chain terminal 195 are shown in FIG. 10K1. There are also etched connections between the white dots such as 200 (FIGS. 10K2 and 10K3) on the back of the LCD chip. These connections are the same for the power, frequency, and PSI LCD 199B and are shown in FIG. 10K3. The connections are slightly different for the suction LCD 199A and are shown in FIG. 10K2.

Most of the electrical parts to produce the circuits described above are common parts, the identity of which unambiguously disclosed by the labels on the figures. The connectors such as the WTB10PR7JTA are made by Airborn, Inc. of Addison, Tex. 75001. The Stancor PPC-3 power transformer may be purchased from Newark Electronics at 1225 North Main, North Canton, Ohio. The suction power amp is an English amplifier designated ILP Y-200 and may be purchased from Gladstone Electronics, 901 Fuhrman Boulevard, Buffalo, N.Y. The Foxboro 1800 transducer and the balance resistors which form part of the suction transducer and are shown in FIG. 10L may be obtained from Foxboro/ICT at 1750 Junction Ave., San Jose, Calif. The PL/IR transducer is an off-the-shelf Foxboro 703 transducer. The suction and PL/IR thermistors 129 and 128 are Oneida GB 1224 thermsistors and may be purchased from Oneida at Box 678 Road 2, Baldwin Extension, Meadville, Pa. 16335. All other parts may be purchased from an electronics distributor such as Canico, Inc. 1355 Shoreway Road, Belmont, Calif. 94002.

The materials from which the various parts of the invention are made are for the most part evident from the functions; we shall briefly review the preferred materials, although it should be understood that many other suitable materials could be used. The PL/IR fluid supply container 15 is formulated out of vinyl plastic as are the various fluid tubes such as 19, 21, 23, and 25. Handpiece 27 is molded out of ABS plastic, and drainage tank 17 is formed from an acrylic plastic. Stand 13 is made of chrome plated steel, and housing 11 is formed of fiberglass. The various threaded screws and rods such as 82A (FIG. 2) are made out of stainless steel while the knurled knobs such as 84A are made of aluminum. The pump bodies, such as 55A, are molded of acrylic resin but ABS plastic, stryene plastic or rigid vinyl would be suitable. Diaphragm 151 is made of soft vinyl, but KRATON TM elastomer or rubber are also suitable. The valves 171 and 173 may be made out of similar materials, although presently KRATON elastomer is used. The pump shafts 67B as well as the flanges such as 65 and 63 are made of acrylic resin, although ABS plastic or styrene are also suitable. In the PL/IR pump (FIG. 8) ball valves 185 are made of ethylene propylene while the springs 186 are made of stainless steel. O-rings 181 are made of soft vinyl, KRATON, or rubber. Filter 175 is made of cotton or foam plastic. The materials of the motor parts shall be discussed in terms of the preferred embodiment of FIG. 14; materials of the embodiment of FIG. 7 will be clear by analogy. The moving coil 213 can be purchased already mounted on cylinder 214 from a source of acoustic speaker parts, such as Quam Nichols, Marquette Road and Prairie Avenue, Chicago, Ill. 60637. Cylinder 214 to which the coil is attached is a piece of thin aluminum (about 0.005 in.). Plates 217 and 221 are made of aluminum, and cylinder 214 is attached to plate 217 by an epoxy adhesive, such as 3M TM brand No. 2214 regular. Shafts 219 are made of aluminum while bushings 227, bosses 223, and post 224 are made of TEFLON TM polytetrafluoroethylene. Spring 225 and the various screws such 222 are made of stainless steel. Magnet 209 is a ceramic magnet and plates 203 and 204 are made of any permeable steel. Housing parts 231 and 233 are preferably made of aluminum for heat dissipation purposes, but also may be made of fiberglass, ABS plastic, etc. as desired. Braided wires 127, 212, and 95 are made of a rope-like fabric that is impregnated with a conductive metal, such as No. P-1603 lead wire available from The Montgomery Company, Canal Bank, Windsor Locks, Conn. 06096.

Turning now to the operation of the system, if the intended use is to be in surgery or other use where sterile or very clean conditions are necessary, all parts of the system that contact the lavage fluid will likely have been removed after the last use, and thus these parts will have to be attached. These parts include the fluid supply bag 15, lines 19, 24A, 24B, 21, 23 and 25, drainage bag 18, couplings 24C and 24D, filter 28, T's 22A and 22B, lavage handpiece 27, and pumps 51A and 51B. All these parts are made out of cheap materials, and all, except perhaps the drainage bag 18, are resterilizable, and thus either a new set of these parts or a set that has been resterilized may be used. The pumps are inserted as shown by the dotted lines in FIG. 6 and the door 74B is closed forcing wedges 75B between fingers 71B causing them to separate and grip flanges 69B and 69B' on pump 51B thereby locking it in place, the door is latched and knob 84A is screwed tight. The distance between flanges 69B and 69B' on pump 51B generally will be made different than the distance between the corresponding flanges 69A and 69A' on pump 51A, with corresponding differences in fingers 71A and 71B, so that a suction pump cannot be inserted in the PL/IR pump chamber and vice versa. All other replaceable parts listed above are attached and the system is primed and checked for leaks prior to surgery or other use. The system is activated by turning switches 31 and 33 to the desired position and knobs 35, 37, 39 and 41 to the desired settings. Settings are chosen by reading meters 119, 117, 121, and 122 respectively rather than setting the position of the knob; this manner of setting allows much more accurate settings than prior art lavage systems.

When switch 31 is in the lavage position, the adjustment of the pulsations per second knob 37 changes the reciprocation frequency of the motor driving pump 51A. Since the power to the pump has not been changed, the pump stroke will change in order that the net power output of the motor remains the same. This results in the average pressure of the fluid flow and the rate of fluid flow remaining the same, providing the response of amplifier 101 is flat with respect to frequency. In the preferred embodiment the response of the amplifiers is flat over the range of about 15 to 35 cps while the frequency range available is between approximately 7 to 40 cycles per second. The rate of flow and pressure will stay constant over the former range and substantially constant over the latter range (providing knob 35 is not moved). By the word substantially it is meant that the rate of flow and the pressure is constant within the normal limits of variation of amplifier output with frequency obtainable with off-the-shelf components. Within this range differences in fluid flow are not readily distinguishable. It has been found for example, that knob 35 may be adjusted to a very low flow level where differences in flow might be more readily distinguishable and knob 37 may be adjusted over the full range without any noticeable changes in rate of flow or pressure. Since in prior art devices the rate of flow would change by a factor of 5 or 6 over this range, the improvement provided by the present invention is considerable.

When switch 31 is in the lavage position, the adjustment of knob 35 changes the power amplifier 101 applies to motor 53a. Since the frequency signal does not change (assuming knob 37 is not moved) the motor responds by changing its stroke length. If the power is increased the motor stroke length is increased and if the power is decreased the stroke length is decreased. The change in stroke length changes the amount of fluid pumped in a given stroke and thus changes both the rate of flow and the pressure. The ability of the motor, and thus the reciprocating pump to change its stroke length in response to a change in power provides a much simpler, more reliable and more efficient means of changing the rate of flow or pressure as compared to the prior art. The embodiment described allows the pressure to be varied from about 1 to 75 PSI and flow rates to be adjusted up to about 1300 ml/min. Other ranges of pressure and flow rates of course may be obtained.

When knob 31 is placed in the irrigation mode, the control of PL/IR pump 51A passes to knob 39. The frequency is set by the "behind the set" control to about 40 cycles per second. Control 39 is calibrated so that a maximum flow rate of about 200 ml/min. is obtained. This provides a somewhat finer control of the flow rate than that obtained with control 35. In this mode, the rate of flow and pressure may be varied without concern about the frequency setting. The ability to switch between a lavage and irrigation mode with knob 31 permits a surgeon to set desired lavage settings with knobs 35 and 37, to switch to irrigation mode without changing the settings of knobs 35 and 37, and then return to the pulsatile lavage mode with the settings already set at their desired positions. It is noted that the irrigation mode settings can be duplicated in the lavage mode, and thus a principal advantage of having the separate irrigation function is that it permits rapid switching between a selected "steady" flow setting and a selected "pulsatile" setting.

The aspiration function may be selected by turning knob 33 to suction, and then adjusting knob 41 for the desired suction rate or vacuum pressure. The range of suction available in the preferred embodiment is from about 1 to 300 mm of mercury which corresponds to a maximum air flow rate of about 45 liters per minute. The frequency of the suction motor is fixed by the "behind the set" control 116 to between 10 and 40 cycles per second with 25 cycles per second being the preferred frequency setting.

It is noted that the invention is not limited to the range of frequencies, pressures, and flow rates of the preferred embodiment. Electronics are available that provide a much wider range of these parameters.

It is noted that because there will be mixtures of air and liquids in suction line 25, the operation of the suction pump 51B will result in cavitation. The pump 51B has been designed to reduce the noise produced by this cavitation. The flexible diaphragm 151 will absorb a certain amount of shock, and the filter 175 also provides a muffling effect.

The setting of the controls will produce the desired type of lavage stream at nozzle 143B and the desired suction at nozzle 143A. The flow of fluid and the suction provided may be controlled directly at the site by use of pinch valves 133 and 135 on lavage handpiece 141. Generally these valves are used for "off" and "on" functions. Valve 133 has been designed so that it will remain in its closed position until it is pushed forward, and valve 135 has been designed so that it will remain at its closed position until serrated arm 137 is lifted to release an open pinch valve 135. In the preferred embodiment, pinch valve 133 is opened by moving pinch valve 133 away from the body of the lavage handpiece 27, while likewise pinch valve 35 moves away from the body 132 of the handpiece 27 when opened. This enables a simultaneous "spreading" movement of pinch valves 133 and 135 to affect a simultaneous opening of both lines 23 and 25. Likewise, when a cessation of operation is desired, a simple squeezing movement of both valves 133 and 135 can be effected. This "outward-inward" operation of the valves facilitates spontaneous operation of the lavage handpiece 27 as a fluid shut-off and attenuation device to augment the system's control board 29.

As described above in connection with the electronics, closure of pinch valve 133 causes the pressure in line 23 to rise, which rise is sensed by transducer 26A and causes the PL/IR motor 53a and pump 51A to shut off. When the valve 133 is released, the pressure in line 23 drops which is again sensed by transducer 26A, which causes the motor 53a and pump 51A to turn on again. In one embodiment potentiometer 35A may be replaced by a dual potentiometer, and one of the pots may be connected to adjust the trip point of the pressure sensing and control circuitry, so that the pressure at which the motor turns off changes as the psi setting is changed; in this embodiment the pressure trip point is maintained about 10 psi above the psi setting of knob 35. This feature provides a remote PL/IR pump control at the lavage site. This remote control is highly efficient when compared to prior art devices, which generally relied totally throttling of the flow to control it. This remote control prevents laboring of the PL/IR pump when 133 is closed, which further reduces the noise of the system and adds significantly to the longevity of the system. It also significantly reduces the risk of bursting pressure lines.

In addition to the shut off of the PL/IR motor by the transducer 26A discussed above, the design of the system also provides a safety feature which limits the maximum pressure in the PL/IR portion of the system and the maximum vacuum in the suction portion of the system. Significantly, this maximum pressure can be adjusted using controls 35, 39 and 41. This feature is provided by the fact that upon application of a given amount of voltage across the coil such as 83 of the motors, a particular magnetic field is set up and consequently a particular force is applied to the piston rods such as 67B. If the fluid pressure acting on the pump, such as 51B, is equal to the force at the piston rod 67B, the piston rod will cease to move. Since the voltage is controllable by knobs 35, 39, and 41, the result is that the maximum pressure and suction provided by the system may be set by these knobs.

After use, the disposable parts mentioned above may be thrown away, or portions of them, such as bag 15 may be thrown away and the other portions resterilized. It is a feature of the invention that the pumps can be easily removed and replaced and that they may be built cheaply, the combination of which makes them disposable. It is noted that the slow speed at which the linear motors generally operate enables the pumps 51A and 51B to be built without the need for precision tolerances, reinforcing, and/or overly strong materials. This factor contributes significantly to the disposability of the pumps. It is further noted that design of pumps 51A and 51B and the connections to and the supports of the pumps enables the pumps to be quickly and easily replaced by persons unskilled in mechanical assembly, with a minimum of directions. In addition, by producing the fluid lines 19, 21, 23, and 25 already connected to the lavage handpiece 27, the fluid supply bag 15 and the pumps 51A and 51B, and by having the remaining connections restricted by their physical dimensions, erroneous connections by operating personnel are avoided.

After use, the drainage tank 17 may be replaced with a sterilized tank, or the tank 17 may be used with a disposable bag 18, which is shown in FIG. 2. This bag permits sanitary reuse of the same drainage tank 17 without sterilization, and facilitates laboratory analysis of the drained material.

It is a feature of the invention that the independent and precise control of the frequency and the flow rate or pressure permits a much broader use of a lavage system under desired medical conditions. For example, the lavage system of the invention may be utilized on a written prescription basis, for example, in a post-operative stage when the actual care is to be administered by nurses or other para-medical personnel who are not as familiar with the reaction of tissues and wounds to excess pressure, or the need for pressure and flow above a certain level in order to ensure a cleansing action.

It should be clear that many of the advantageous features discussed above are possible to include in the system as a result of the fact that the motive force of the system is provided by a linear motor, and in particular a moving coil linear motor. The moving coil motor is generally known to be a quickly responsive motor, due to the fact that it has relatively small inertia in its moving parts. Because the drive member parts such as plates 217 and 221 and shafts 219 are made of a light weight material, the motor of the invention retains most of its responsiveness, but it has developed that other properties of the motor are significant in producing the unexpectedly good results achieved by combining the linear motor with a lavage system.

As mentioned above, the motor lends itself to a simple and effective means of controlling the volume of fluid flow, because its stroke length is easily variable. The fact discussed above that the stroke length changes as the frequency changes so that flow and pressure remain constant has turned out to be a significant feature in the lavage system.

One reason that prior art moving coil linear motors have not been considered as useful for functions requiring significant force relates to the fact that, like nearly all motors, they produce a varying power along their stroke. Rotary motors develop an inertia that enables them to resist stalling at the point of low power. However, in linear motors the points of lowest power are at the ends of its stroke, where its direction changes and its inertia is at or near zero. The springs, 90, 93, and 225 produce a restoring force that reaches its maximum at the ends of the stroke of the motor. This restoring force prevents the motor from stalling at the point where its direction changes. The springs also produce some force resisting motion of the coil near its central position, which resistance is not desirable. The varying coil springs 225 increase the restoring force at the ends of the stroke and at the same time reduce the force acting against the coil 213 near the central position. The addition of the variable damping springs also permits the motor to handle large amounts of electrical power, and produce correspondingly high mechanical power, without slamming up against the end stops, which would be quite noisy and ultimately damages the motor. This feature results in a much more powerful yet quieter running and more reliable motor than previous linear motors. In addition, the springs permit longer excursions of the stroke of the motor leading to more volume control and more cooling effect, which shall be discussed below. The varying coil spacing adds to these beneficial effects by increasing damping at the limits of excursion and decreasing damping in the central position.

The addition of the shafts and bearings to the motor greatly increases the stability of the motor. The stability is particularly noted under heavy load, a condition which in prior art linear motors would result in rubbing of the moving part, which in this case is the coil, in its slot. Thus the use of the journal permits the use of a much narrower slot for the coil to move in, which increases the power available from the motor because it keeps the magnetic fields of the coil and core close together, thus increasing their interaction.

The structure of the drive member, such as 216, also contributes to the ability of the motor to handle large loads. The shafts, such as 219, act as a cooling means for the motor. The aluminum out of which they are made is a very good heat conductor. Since the plate 217 is in close contact with the coil and the shafts are in close contact with the core through the bearings 227, they serve to dissipate the heat produced in the coil and core. The end plates 217 and 221 are excellent heat radiators. The fact that they are moving creates a fanning effect on the motor. The end result is reduced and uniform temperatures throughout the motor, which also contributes to the ability to maintain close moving tolerances. The use of three shafts in the preferred embodiment prevents rocking or canting of the coil under heavy loads, again contributing to close tolerances.

The design, particularly the fact that the shafts 89 and 219 pass through the core 86 and 209, provides a very compact motor. The compactness leads to the scaling down of the supports, housing and related parts of the system, which makes it possible to mount the whole system on a pole, keeping it out of the way of the physician and allowing it to be wheeled in and out of the work area as needed.

The motor of the invention is an unusually small, powerful and efficient linear motor. When combined with a lavage system, the variable stroke length adds a further element of efficiency. The efficiency is significant in that it results in many benefits which make the system very welcome in the hospital: lower noise, lower heat output, and the fact that no fan is needed. Fans are particularly unwelcome in surgery because they circulate bacteria as well as air.

A novel system that for the first time combines a linear motor with a system with lavage functions, leading to numerous features and advantages, has been disclosed. While the above description of the invention has been referenced to a few particular embodiments, it is evident that, now that the advantages of a lavage system with a linear motor have been disclosed, those skilled in the art can now make numerous uses of, modifications of, and departures from the specific embodiments described herein without departing from the inventive concepts. For example, the system could be simplified to provide only one of any of the three lavage functions (pulsatile lavage, irrigation, and aspiration), or it may be expanded to include a pulsatile aspiration function, in addition to the other functions, or any combination of the functions. It is also anticipated that other features may be combined with the invention. For example, many different lavage handpieces may be substituted for the handpiece 27, or many different nozzles may be substituted for the nozzles 143A and 143B or, sources of fluid other than container 15 may be provided. It is clear that now that the principles of the invention have been disclosed, most of the system may be replaced by equivalent parts; for example: the magnets 209 and 79 could be replaced with any means for producing a constantly polarized magnetic field while the motor is running, such as an electromagnet; other variable damping means could be substituted, for example, springs with a varying wire thickness, or springs with a varying coil diameter (conical springs) could be used; other drive means could be substituted; a wide variety of equivalent electronic circuits are available that could be substituted for those shown. Consequently, the invention is to be construed as embracing each and every novel feature and novel combination of features within the appended claims.

What I claim is:

1. Medical, dental or therapeutic lavage apparatus comprising:
   a chamber having an inlet port and an outlet port;
   a reciprocating means for imparting a pulsatile flow to liquid moving from the inlet port to the outlet port;
   a linear electric motor having a drive member;
   means for supporting said motor and said chamber in stable relationship;
   means for connecting the motor drive member to said reciprocating means to produce said pulsatile flow;
   means for producing an electrical power signal and for applying said signal to said motor;
   means for varying the frequency of said power signal, said means including a manually settable frequency control; and
   means for varying the amplitude of said power signal, said means including a manually settable amplitude control.

2. Lavage apparatus as in claim 1 wherein said motor comprises a moveable coil and a stationary core, with the coil connected to said drive member.

3. Lavage apparatus as in claim 2, wherein said motor drive member includes a shaft and a bearing, said shaft being moveable in said bearing and passing through said motor core.

4. Lavage apparatus as in claim 3, wherein there are three shafts and three bearings.

5. Lavage apparatus as in claim 4, wherein said drive member further includes:
   a first connecting member to which said coil and one of said shafts are connected;
   a second connecting member to which the other end of said shafts are connected;
   and said shafts and bearings being spaced apart along a circle about the axis of said coil.

6. Lavage apparatus as in claim 5 and further comprising a pair of coil springs having varying coil spacing, one spring of each pair extending between the first connecting member and motor core and the other spring of each pair extending between the second connecting member and the motor core.

7. Lavage apparatus as in claim 2 and further comprising a means for variably damping the motion of said coil, said means providing minimum damping when the coil is positioned at the center of its reciprocating path and for providing maximum damping when the coil is located at the end points of its motion in either direction.

8. Lavage apparatus as in claim 7, wherein said means for damping comprises at least one coil spring having variable coil spacing.

9. Lavage apparatus as in claim 1 and further comprising:
   means for fixing the frequency of said signal at a predetermined frequency; and
   a switch having a first position in which said means for varying the frequency is enabled to control said power signal, and a second position in which said means for fixing the frequency is enabled to control said power signal.

10. Lavage apparatus as in claim 9, wherein said means for varying the amplitude of said signal comprises:
a first manually settable amplitude control for controlling the amplitude;
a second manually settable amplitude control for controlling the amplitude; and
said switch further comprises means for switching control of the amplitude to said first amplitude control when said switch is in said first position, and for switching control of the amplitude to said second control when said switch is in said second position.

11. Lavage apparatus as in claim 2, wherein said motor core includes a stationary permanent magnet.

12. Lavage apparatus as in claim 1, wherein:
said motor includes a motor core: and
said drive member includes three shafts and three bearings, said shafts moveable in said bearings and passing through the motor core.

* * * * *